US007615569B2

(12) United States Patent
Fulp et al.

(10) Patent No.: US 7,615,569 B2
(45) Date of Patent: Nov. 10, 2009

(54) INHIBITORS OF ION CHANNELS

(75) Inventors: Alan Fulp, Willow Springs, NC (US);
Brian Marron, Durham, NC (US);
Mark J. Suto, Chapel Hill, NC (US);
Xiaodong Wang, Jiangyin (CN)

(73) Assignee: Icagen, Inc., Durham, NC (US)

( * ) Notice: Subject to any disclaimer, the term of this patent is extended or adjusted under 35 U.S.C. 154(b) by 273 days.

(21) Appl. No.: 11/464,057

(22) Filed: Aug. 11, 2006

(65) Prior Publication Data

US 2007/0078145 A1    Apr. 5, 2007

Related U.S. Application Data

(60) Provisional application No. 60/708,866, filed on Aug. 16, 2005.

(51) Int. Cl.
*A61K 31/427* (2006.01)
*A61K 31/513* (2006.01)
*C07D 283/02* (2006.01)
*C07D 277/52* (2006.01)
*C07D 277/28* (2006.01)
*C07D 403/10* (2006.01)

(52) U.S. Cl. .................. 514/370; 514/274; 514/365; 548/197; 548/205; 544/310

(58) Field of Classification Search ............... 548/193; 544/310; 514/274, 370, 365
See application file for complete search history.

(56) References Cited

U.S. PATENT DOCUMENTS 6,262,078 B1    7/2001    Loughhead et al.

OTHER PUBLICATIONS

Priest et al. PNAS 2007, 104(20), 8205-8206.*

Chaplan, S.R., et al., "Quantitative Assessment of Tactile Allodynia in the Rat Paw," *J. Neurosci. Methods*, 53:55-63 (1994).

Devor, et al.,"$Na^{30}$ Channel Immunolocalization in Peripheral Mammalian Axons and Changes Following Nerve Injury and Neuroma Formation," *J. Neurosci.*, 13(5):1976-1992 (May 1993).

Kim, et al., "An Experimental Model for Peripheral Neuropathy Produced by Segmental Spinal Nerve Ligation in the Rat," *Pain*, 50:355-363 (1992).

Legroux-Crespel, E., et al., "Traitement de L'érythermalgie Familiale Par L'association Liodocaïne- Mexilétine," *Ann. Dermatol. Venereal*, 130:429-33 (2003).

Srivatsa, U. et al., "Mechanisms of Antiarrhythmic Drug Actions and Their Clinical Relevance for Controlling Disorders of Cardiac Rhythm," *Curr. Cardiol. Rep.*, 4(5):401-410 (Sep. 4, 2002).

Toledo-Aral, et al., "Identification of PN1, a Predominant Voltage-Dependent Sodium Channel Expressed Principally in Peripheral Neurons," *Proc. Natl. Acad. Sci. USA*, 94:1527-1532 (Feb. 1997).

Wood, J., et al., "Voltage-Gated Sodium Channels and Pain Pathways," *J. Neurobiol.*, 61(1):55-71 (Oct. 2004).

* cited by examiner

*Primary Examiner*—Rebecca L Anderson
*Assistant Examiner*—Jason Nolan
(74) *Attorney, Agent, or Firm*—Townsend and Townsend and Crew LLP

(57) ABSTRACT

Compounds, compositions and methods are provided which are useful in the treatment of diseases through the inhibition of sodium ion flux through voltage-gated sodium channels. More particularly, the invention provides heterocyclic aryl sulfonamides, compositions and methods that are useful in the treatment of central or peripheral nervous system disorders, particularly pain and chronic pain by blocking sodium channels associated with the onset or recurrence of the indicated conditions. The compounds, compositions and methods of the present invention are of particular use for treating neuropathic or inflammatory pain by the inhibition of ion flux through a voltage-gated sodium channel.

13 Claims, 11 Drawing Sheets

| Compound Number | Compound Name |
|---|---|
| 1. | 4-(4,5-Diphenyl-1H-imidazol-2-yl)-N-thiazol-2-yl-benzenesulfonamide |
| 2. | 4-(5-Phenyl-1H-imidazol-2-yl)-N-thiazol-2-yl-benzenesulfonamide |
| 3. | 4-(5-Benzhydryl-4H-[1,2,4]triazol-3-yl)-N-thiazol-2-yl-benzenesulfonamide |
| 4. | 4-(4-Methyl-5-phenyl-1H-imidazol-2-yl)-N-thiazol-2-yl-benzenesulfonamide |
| 5. | 4-(5-Hydroxymethyl-1H-imidazol-2-yl)-N-thiazol-2-yl-benzenesulfonamide |
| 6. | 4-(5-Benzhydryl-1H-imidazol-2-yl)-N-thiazol-2-yl-benzenesulfonamide |
| 7. | 4-[5-(3,5-Difluoro-benzyl)-1H-imidazol-2-yl]-N-thiazol-2-yl-benzenesulfonamide |
| 8. | 4-[5-(4-Chloro-benzyl)-1H-imidazol-2-yl]-N-thiazol-2-yl-benzenesulfonamide |
| 9. | 4-{4-[3-(4-Chloro-phenoxy)-propyl]-1H-imidazol-2-yl}-N-thiazol-2-yl-benzenesulfonamide |
| 10. | 4-(1H-Benzoimidazol-2-yl)-N-thiazol-2-yl-benzenesulfonamide |
| 11. | 4-{4-[3-(2,4-Dichloro-phenoxy)-propyl]-1H-imidazol-2-yl}-N-thiazol-2-yl-benzenesulfonamide |
| 12. | 4-{4-[4-(4-Chloro-phenyl)-cyclohexyl]-1H-imidazol-2-yl}-N-thiazol-2-yl-benzenesulfonamide |

FIG. 1A

| Compound Number | Compound Name |
|---|---|
| 13. | 4-[4-(2-Chloro-4-fluoro-benzyl)-1H-imidazol-2-yl]-N-thiazol-2-yl-benzenesulfonamide |
| 14. | 4-{4-[2-(2-Chloro-phenyl)-ethyl]-1H-imidazol-2-yl}-N-thiazol-2-yl-benzenesulfonamide |
| 15. | 4-{4-[2-(4-Fluoro-phenyl)-ethyl]-1H-imidazol-2-yl}-N-thiazol-2-yl-benzenesulfonamide |
| 16. | 4-[4-(3-Chloro-benzyl)-1H-imidazol-2-yl]-N-thiazol-2-yl-benzenesulfonamide |
| 17. | N-Thiazol-2-yl-4-[4-(2-p-tolyl-ethyl)-1H-imidazol-2-yl]-benzenesulfonamide |
| 18. | 4-{4-[2-(3-Chloro-4-methoxy-phenyl)-ethyl]-1H-imidazol-2-yl}-N-thiazol-2-yl-benzenesulfonamide |
| 19. | N-Thiazol-2-yl-4-{4-[2-(4-trifluoromethyl-phenyl)-ethyl]-1H-imidazol-2-yl}-benzenesulfonamide |
| 20. | 4-{4-[2-(3,5-Bis-trifluoromethyl-phenyl)-ethyl]-1H-imidazol-2-yl}-N-thiazol-2-yl-benzenesulfonamide |
| 21. | N-Thiazol-2-yl-4-[4-(1-p-tolyl-cyclohexyl)-1H-imidazol-2-yl]-benzenesulfonamide |
| 22. | 4-{4-[2-(2,5-Bis-trifluoromethyl-phenyl)-ethyl]-1H-imidazol-2-yl}-N-thiazol-2-yl-benzenesulfonamide |

FIG. 1B

| Compound Number | Compound Name |
|---|---|
| 23. | 4-[4-(3,4-Difluoro-benzyl)-1H-imidazol-2-yl]-N-thiazol-2-yl-benzenesulfonamide |
| 24. | 4-(4-Pentafluorophenylmethyl-1H-imidazol-2-yl)-N-thiazol-2-yl-benzenesulfonamide |
| 25. | 4-{4-[1-(4-Chloro-phenyl)-cyclobutyl]-1H-imidazol-2-yl}-N-thiazol-2-yl-benzenesulfonamide |
| 26. | 4-{4-[2-(3,5-Dichloro-phenyl)-ethyl]-1H-imidazol-2-yl}-N-thiazol-2-yl-benzenesulfonamide |
| 27. | 4-[4-(3-Methyl-benzyl)-1H-imidazol-2-yl]-N-thiazol-2-yl-benzenesulfonamide |
| 28. | 4-{4-[2-(3-Chloro-phenyl)-ethyl]-1H-imidazol-2-yl}-N-thiazol-2-yl-benzenesulfonamide |
| 29. | 4-{4-[2-(2,5-Dimethyl-phenyl)-ethyl]-1H-imidazol-2-yl}-N-thiazol-2-yl-benzenesulfonamide |
| 30. | 4-[4-(3-Fluoro-benzyl)-1H-imidazol-2-yl]-N-thiazol-2-yl-benzenesulfonamide |
| 31. | 4-[4-(2,5-Difluoro-benzyl)-1H-imidazol-2-yl]-N-thiazol-2-yl-benzenesulfonamide |
| 32. | 4-[4-(4-Methyl-benzyl)-1H-imidazol-2-yl]-N-thiazol-2-yl-benzenesulfonamide |

FIG. 1C

| Compound Number | Compound Name |
|---|---|
| 33. | N-Thiazol-2-yl-4-[4-(2-o-tolyl-ethyl)-1H-imidazol-2-yl]-benzenesulfonamide |
| 34. | N-Thiazol-2-yl-4-[4-(4-trifluoromethyl-benzyl)-1H-imidazol-2-yl]-benzenesulfonamide |
| 35. | 4-[4-(2-Fluoro-benzyl)-1H-imidazol-2-yl]-N-thiazol-2-yl-benzenesulfonamide |
| 36. | 4-[4-(3,4-Dichloro-benzyl)-1H-imidazol-2-yl]-N-thiazol-2-yl-benzenesulfonamide |
| 37. | 4-{4-[2-(2-Fluoro-phenyl)-ethyl]-1H-imidazol-2-yl}-N-thiazol-2-yl-benzenesulfonamide |
| 38. | N-Thiazol-2-yl-4-{4-[2-(3-trifluoromethyl-phenyl)-ethyl]-1H-imidazol-2-yl}-benzenesulfonamide |
| 39. | 4-[4-(2,4-Difluoro-benzyl)-1H-imidazol-2-yl]-N-thiazol-2-yl-benzenesulfonamide |
| 40. | 4-[4-(2,6-Difluoro-benzyl)-1H-imidazol-2-yl]-N-thiazol-2-yl-benzenesulfonamide |
| 41. | 4-[4-(1-Phenyl-cyclopropyl)-1H-imidazol-2-yl]-N-thiazol-2-yl-benzenesulfonamide |
| 42. | 4-[4-(4-Phenoxy-benzyl)-1H-imidazol-2-yl]-N-thiazol-2-yl-benzenesulfonamide |
| 43. | N-Thiazol-2-yl-4-[4-(3-trifluoromethoxy-benzyl)-1H-imidazol-2-yl]-benzenesulfonamide |
| 44. | 4-{4-[1-(4-Methoxy-phenyl)-cyclopropyl]-1H-imidazol-2-yl}-N-thiazol-2-yl-benzenesulfonamide |

FIG. 1D

| Compound Number | Compound Name |
|---|---|
| 45. | 4-[4-(2-Methoxy-benzyl)-1H-imidazol-2-yl]-N-thiazol-2-yl-benzenesulfonamide |
| 46. | 4-(4-Benzyl-1H-imidazol-2-yl)-N-thiazol-2-yl-benzenesulfonamide |
| 47. | 4-[4-(Cyclohexyl-phenyl-methyl)-1H-imidazol-2-yl]-N-thiazol-2-yl-benzenesulfonamide |
| 48. | 4-[4-(1-Phenyl-propyl)-1H-imidazol-2-yl]-N-thiazol-2-yl-benzenesulfonamide |
| 49. | 4-(4-Benzo[1,3]dioxol-5-ylmethyl-1H-imidazol-2-yl)-N-thiazol-2-yl-benzenesulfonamide |
| 50. | 4-[4-(3-Methoxy-benzyl)-1H-imidazol-2-yl]-N-thiazol-2-yl-benzenesulfonamide |
| 51. | N-Thiazol-2-yl-4-[4-(2-trifluoromethyl-benzyl)-1H-imidazol-2-yl]-benzenesulfonamide |
| 52. | 4-[4-(2-Methyl-1-phenyl-propyl)-1H-imidazol-2-yl]-N-thiazol-2-yl-benzenesulfonamide |
| 53. | 4-(4-{3-[2,4-Bis-(1,1-dimethyl-propyl)-phenoxy]-propyl}-1H-imidazol-2-yl)-N-thiazol-2-yl-benzenesulfonamide |
| 54. | 4-[4-(4-Methanesulfonyl-benzyl)-1H-imidazol-2-yl]-N-thiazol-2-yl-benzenesulfonamide |
| 55. | 4-[4-(1-Methyl-1-phenyl-ethyl)-1H-imidazol-2-yl]-N-thiazol-2-yl-benzenesulfonamide |
| 56. | 4-[4-(3-Bromo-benzyl)-1H-imidazol-2-yl]-N-thiazol-2-yl-benzenesulfonamide |

FIG. 1E

| Compound Number | Compound Name |
|---|---|
| 57. | 4-(5-Benzyl-4H-[1,2,4]triazol-3-yl)-N-thiazol-2-yl-benzenesulfonamide |
| 58. | 4-[5-(3-Phenoxy-benzyl)-1H-imidazol-2-yl]-N-thiazol-2-yl-benzenesulfonamide |
| 59. | 4-[4-(Cyclopentyl-phenyl-methyl)-1H-imidazol-2-yl]-N-thiazol-2-yl-benzenesulfonamide |
| 60. | 4-{4-[1-(4-Chloro-phenyl)-cyclopentyl]-1H-imidazol-2-yl}-N-thiazol-2-yl-benzenesulfonamide |
| 61. | 4-[5-(3-Benzyloxy-benzyl)-1H-imidazol-2-yl]-N-thiazol-2-yl-benzenesulfonamide |
| 62. | 4-[4-(2-Bromo-benzyl)-1H-imidazol-2-yl]-N-thiazol-2-yl-benzenesulfonamide |
| 63. | 4-(4-Bicyclo[4.2.0]octa-1(6),2,4-trien-7-ylmethyl-1H-imidazol-2-yl)-N-thiazol-2-yl-benzenesulfonamide |
| 64. | 4-[4-(1,1-Diphenyl-ethyl)-1H-imidazol-2-yl]-N-thiazol-2-yl-benzenesulfonamide |
| 65. | 4-[4-(2-Chloro-6-fluoro-benzyl)-1H-imidazol-2-yl]-N-thiazol-2-yl-benzenesulfonamide |
| 66. | 4-[4-(2,6-Dichloro-benzyl)-1H-imidazol-2-yl]-N-thiazol-2-yl-benzenesulfonamide |
| 67. | N-Thiazol-2-yl-4-{4-[4-(2,2,2-trifluoro-ethyl)-benzyl]-1H-imidazol-2-yl}-benzenesulfonamide |
| 68. | 4-{4-[2-(3,5-Dichloro-phenyl)-ethyl]-5-iodo-1H-imidazol-2-yl}-N-thiazol-2-yl-benzenesulfonamide |

FIG. 1F

| Compound Number | Compound Name |
|---|---|
| 69. | 2-(4-{4-[2-(3,5-Dichloro-phenyl)-ethyl]-1H-imidazol-2-yl}-benzenesulfonylmethyl)-5-iodo-thiazole |
| 70. | 2-(4-{4-[2-(3,5-Dichloro-phenyl)-ethyl]-5-iodo-1H-imidazol-2-yl}-benzenesulfonylmethyl)-5-iodo-thiazole |
| 71. | 4-{4-[2-(4-Fluoro-phenyl)-1-phenyl-ethyl]-1H-imidazol-2-yl}-N-thiazol-2-yl-benzenesulfonamide |
| 72. | 4-[4-(2-Chloro-6-fluoro-3-methyl-benzyl)-1H-imidazol-2-yl]-N-thiazol-2-yl-benzenesulfonamide |
| 73. | 4-[4-(3-Chloro-2-fluoro-benzyl)-1H-imidazol-2-yl]-N-thiazol-2-yl-benzenesulfonamide |
| 74. | N-Thiazol-2-yl-4-[4-(3-trifluoromethyl-benzyl)-1H-imidazol-2-yl]-benzenesulfonamide |
| 75. | 4-[4-(2,4-Dichloro-5-fluoro-benzyl)-1H-imidazol-2-yl]-N-thiazol-2-yl-benzenesulfonamide |
| 76. | 4-[4-(2-Bromo-5-chloro-benzyl)-1H-imidazol-2-yl]-N-thiazol-2-yl-benzenesulfonamide |
| 77. | 4-[4-(5-Chloro-2-trifluoromethyl-benzyl)-1H-imidazol-2-yl]-N-thiazol-2-yl-benzenesulfonamide |
| 78. | 4-[4-(4-Bromo-benzyl)-1H-imidazol-2-yl]-N-thiazol-2-yl-benzenesulfonamide |
| 79. | 4-[4-(3-Bromo-4-fluoro-benzyl)-1H-imidazol-2-yl]-N-thiazol-2-yl-benzenesulfonamide |
| 80. | 4-[4-(2-Methyl-benzyl)-1H-imidazol-2-yl]-N-thiazol-2-yl-benzenesulfonamide |

FIG. 1G

| Compound Number | Compound Name |
|---|---|
| 81. | 4-[4-(2,3-Difluoro-benzyl)-1H-imidazol-2-yl]-N-thiazol-2-yl-benzenesulfonamide |
| 82. | 4-[4-(2-Chloro-benzyl)-1H-imidazol-2-yl]-N-thiazol-2-yl-benzenesulfonamide |
| 83. | 4-[4-(2-Chloro-3-fluoro-benzyl)-1H-imidazol-2-yl]-N-thiazol-2-yl-benzenesulfonamide |
| 84. | N-(5-Chloro-thiazol-2-yl)-4-{4-[2-(3,5-dichloro-phenyl)-ethyl]-1H-imidazol-2-yl}-benzenesulfonamide |
| 85. | 4-[4-(3,5-Difluoro-benzyl)-1H-imidazol-2-yl]-N-pyridin-2-ylmethyl-benzenesulfonamide |
| 86. | 4-[4-(2-Chloro-4-trifluoromethyl-benzyl)-1H-imidazol-2-yl]-N-thiazol-2-yl-benzenesulfonamide |
| 87. | 4-[4-(4-Chloro-3-fluoro-benzyl)-1H-imidazol-2-yl]-N-thiazol-2-yl-benzenesulfonamide |
| 88. | 4-[4-(2-Fluoro-4-trifluoromethyl-benzyl)-1H-imidazol-2-yl]-N-thiazol-2-yl-benzenesulfonamide |
| 89. | 4-[4-(4-Fluoro-2-trifluoromethyl-benzyl)-1H-imidazol-2-yl]-N-thiazol-2-yl-benzenesulfonamide |
| 90. | 4-[4-(3-Chloro-2,6-difluoro-benzyl)-1H-imidazol-2-yl]-N-thiazol-2-yl-benzenesulfonamide |
| 91. | 4-{4-[1-(2-Fluoro-biphenyl-4-yl)-ethyl]-1H-imidazol-2-yl}-N-thiazol-2-yl-benzenesulfonamide |
| 92. | 4-{4-[1-(4-Isobutyl-phenyl)-ethyl]-1H-imidazol-2-yl}-N-thiazol-2-yl-benzenesulfonamide |

FIG. 1H

| Compound Number | Compound Name |
|---|---|
| 93. | 4-[4-(5-Fluoro-2-trifluoromethyl-benzyl)-1H-imidazol-2-yl]-N-thiazol-2-yl-benzenesulfonamide |
| 94. | 4-[4-(6-Chloro-2-fluoro-3-methyl-benzyl)-1H-imidazol-2-yl]-N-thiazol-2-yl-benzenesulfonamide |
| 95. | 4-[5-(3,4-Dichloro-benzyl)-4H-[1,2,4]triazol-3-yl]-N-thiazol-2-yl-benzenesulfonamide |
| 96. | 4-[5-(3-Chloro-benzyl)-4H-[1,2,4]triazol-3-yl]-N-thiazol-2-yl-benzenesulfonamide |
| 97. | 4-[5-(3,4-Dichloro-benzyl)-4-methoxymethyl-4H-[1,2,4]triazol-3-yl]-N-thiazol-2-yl-benzenesulfonamide |
| 98. | 4-[4-(3,5-Difluoro-benzyl)-1H-imidazol-2-yl]-N-thiazol-2-ylmethyl-benzenesulfonamide |
| 99. | 4-[3-(3,4-Dichloro-benzyl)-4-methyl-2,5-dioxo-imidazolidin-4-yl]-N-thiazol-2-yl-benzenesulfonamide |
| 100. | 4-[1-(3,4-Dichloro-benzyl)-4-methyl-2,5-dioxo-imidazolidin-4-yl]-N-thiazol-2-yl-benzenesulfonamide |
| 101. | 4-[3-(3,4-Dichloro-benzyl)-2,5-dioxo-imidazolidin-4-yl]-N-thiazol-2-yl-benzenesulfonamide |
| 102. | 4-[1-(3,4-Dichloro-benzyl)-2,5-dioxo-imidazolidin-4-yl]-N-thiazol-2-yl-benzenesulfonamide |
| 103. | 4-[4-(3,4-Dichloro-benzyl)-5-oxo-4,5-dihydro-1H-[1,2,4]triazol-3-yl]-N-thiazol-2-yl-benzenesulfonamide |
| 104. | 4-[1-(3,4-Dichloro-benzyl)-5-oxo-2,5-dihydro-1H-pyrazol-3-yl]-N-thiazol-2-yl-benzenesulfonamide |

FIG. 1I

| Compound Number | Compound Name |
|---|---|
| 105. | 4-[4-(3,4-Dichloro-benzyl)-5-oxo-2,5-dihydro-1H-pyrazol-3-yl]-N-thiazol-2-yl-benzenesulfonamide |
| 106. | 4-[4-(3,4-Dichloro-benzyl)-5-oxo-4,5-dihydro-1H-imidazol-2-yl]-N-thiazol-2-yl-benzenesulfonamide |
| 107. | 4-[4-(3,4-Dichloro-benzyl)-4-methyl-5-oxo-4,5-dihydro-1H-imidazol-2-yl]-N-thiazol-2-yl-benzenesulfonamide |
| 108. | 4-[1-(3,4-Dichloro-benzyl)-2,6-dioxo-1,2,3,6-tetrahydro-pyrimidin-4-yl]-N-thiazol-2-yl-benzenesulfonamide |
| 109. | 4-[3-(3,5-Dichloro-benzyl)-2,6-dioxo-1,2,3,6-tetrahydro-pyrimidin-4-yl]-N-thiazol-2-yl-benzenesulfonamide |
| 110. | 4-[5-(3,4-Dichloro-benzoyl)-4H-[1,2,4]triazol-3-yl]-N-thiazol-2-yl-benzenesulfonamide |
| 111. | 4-[2-(3,4-Dichloro-benzyl)-3H-imidazol-4-yl]-N-thiazol-2-yl-benzenesulfonamide |
| 112. | 4-[2-(3,4-Dichloro-benzyl)-5-oxo-4,5-dihydro-3H-imidazol-4-yl]-N-thiazol-2-yl-benzenesulfonamide |
| 113. | 4-[2-(3,4-Dichloro-benzyl)-4-methyl-5-oxo-4,5-dihydro-3H-imidazol-4-yl]-N-thiazol-2-yl-benzenesulfonamide |
| 114. | 4-[5-(4-Chloro-benzyl)-2H-[1,2,4]triazol-3-yl]-2-fluoro-n-thiazol-2-yl-benzenesulfonamide |
| 115. | 4-[5-(2,6-Dichloro-phenoxymethyl)-2H-[1,2,4]triazol-3-yl]-2-fluoro-n-thiazol-2-yl-benzenesulfonamide |
| 116. | 4-[5-(3-Chloro-5-trifluoromethyl-pyridin-2-yl)-2H-[1,2,4]triazol-3-yl]-2-fluoro-n-thiazol-2-yl-benzenesulfonamide |

FIG. 1J

| Compound Number | Compound Name |
|---|---|
| 117. | 4-[5-(3-Chloro-5-trifluoromethyl-pyridin-2-yloxymethyl)-2H-[1,2,4]triazol-3-yl]-n-thiazol-2-yl-benzenesulfonamide |
| 118. | N-thiazol-2-yl-4-[5-(5-trifluoromethyl-pyridin-2-yloxymethyl)-4H-[1,2,4]triazol-3-yl]-benzenesulfonamide |
| 119. | 4-[5-(2,6-Dichloro-phenoxymethyl)-2H-[1,2,4]triazol-3-yl]-n-thiazol-2-yl-benzenesulfonamide |
| 120. | 4-[5-(3,5-Dichloro-pyridin-2-yloxymethyl)-4H-[1,2,4]triazol-3-yl]-n-thiazol-2-yl-benzenesulfonamide |
| 121. | 4-[5-(2-pyridin-3-yl-ethyl)-2H-[1,2,4]triazol-3-yl]-n-thiazol-2-yl-benzenesulfonamide |
| 122. | 5-Chloro-2-(4-{4-[2-(3,5-dichloro-phenyl)-ethyl]-1H-imidazol-2-yl}-benzenesulfonylmethyl)-thiazole |
| 123. | 4-{5-[3-(2,4-Dichloro-phenoxy)-propyl]-1H-pyrazol-3-yl}-N-thiazol-2-yl-benzenesulfonamide |
| 124. | 6-(2,2-Diphenyl-ethylamino)-pyridine-3-sulfonic acid thiazol-2-ylamide |

FIG. 1K

INHIBITORS OF ION CHANNELS

CROSS-REFERENCE TO RELATED APPLICATIONS

This application claims priority to U.S. Provisional Application No. 60/708,866, filed on Aug. 16, 2005, the disclosure of which is incorporated herein in its entirety for all purposes.

This invention relates to the use of certain compounds as sodium channel blockers and to the treatment of pain by the inhibition of sodium channels. Additionally, this invention relates to novel compounds that are useful as sodium channel blockers.

BACKGROUND OF THE INVENTION

Voltage-gated sodium channels are found in all excitable cells including myocytes of muscle and neurons of the central and peripheral nervous system. In neuronal cells sodium channels are primarily responsible for generating the rapid upstroke of the action potential. In this manner sodium channels are essential to the initiation and propagation of electrical signals in the nervous system. Proper and appropriate function of sodium channels is therefore necessary for normal function of the neuron. Consequently, aberrant sodium channel function is thought to underlie a variety of medical disorders (See Hubner C A, Jentsch T J, *Hum Mol Genet.* 2002 Oct. 1; 11(20):2435-45 for a general review of inherited ion channel disorders) including epilepsy (Yogeeswari et al., *Curr Drug Targets.* 2004 October; 5(7):589-602), arrhythmia (Noble D., *Proc Natl Acad Sci U.S.A.* 2002 Apr. 30; 99 (9): 5755-6) myotonia (Cannon, S C *Kidney Int.* 2000 March; 57(3):772-9), and pain (Wood, J N et al., *J Neurobiol.* 2004 October; 61(1):55-71). See Table I, below.

The remaining TTX-resistant sodium channels, Nav1.8 (SCN10A, PN3, SNS) and Nav1.9 (SCN11A, NaN, SNS2) are expressed in the peripheral nervous system and show preferential expression in primary nociceptive neurons. Human genetic variants of these channels have not been associated with any inherited clinical disorder. However, aberrant expression of Nav1.8 has been found in the CNS of human multiple sclerosis (MS) patients and also in a rodent model of MS (Black, J A, et al *Proc Natl Acad Sci USA.* 2000 Oct. 10; 97(21):11598-602). Evidence for involvement in nociception is both associative (preferential expression in nociceptive neurons) and direct (genetic knockout). Nav1.8-null mice exhibited typical nociceptive behavior in response to acute noxious stimulation but had significant deficits in referred pain and hyperalgesia (Laird J M, et al., *J Neurosci.* 2002 Oct. 1; 22(19):8352-6).

The TTX-sensitive subset of voltage-gated sodium channels is expressed in a broader range of tissues than the TTX-resistant channels and has been associated with a variety of human disorders. The $Na_v1.1$ channel well exemplifies this general pattern, as it is expressed in both the central and peripheral nervous system and has been associated with several seizure disorders including Generalized Epilepsy with Febrile Seizures Plus, types 1 and 2 (GEFS+1, GEFS+2), Severe Myoclonic Epilepsy of Infancy (SMEI), and others (Claes, L, et al., *Am. J. Hum. Genet.* 68: 1327-1332, 2001; Escayg, A., *Am. J. Hum. Genet.* 68: 866-873, 2001: Lossin, C, *Neuron* 34: 877-884, 2002). The Nav1.2 channel is largely, if not exclusively, expressed in the central nervous system and quantitative studies indicate it is the most abundant VGSC of the CNS. Mutations of Nav1.2 are also associated with seizure disorders (Berkovic, S. F., et al., *Ann. Neurol.* 55: 550-557, 2004) and Nav1.2-null "knockout" mice exhibit perina-

TABLE I

| Type | Gene Symbol | Primary tissue | TTX IC-50 | Disease association | Indications |
| --- | --- | --- | --- | --- | --- |
| $Na_v1.1$ | SCN1A | CNS/PNS | 10 | Epilepsy | Pain, seizures, neurodegeneration |
| $Na_v1.2$ | SCN2A | CNS | 10 | Epilepsy | Epilepsy, neurodegeneration |
| $Na_v1.3$ | SCN3A | CNS | 15 | — | Pain |
| $Na_v1.4$ | SCN4A | Sk. muscle | 25 | Myotonia | Myotonia |
| $Na_v1.5$ | SCN5A | Heart | 2000 | Arrhythmia | Arrhythmia |
| $Na_v1.6$ | SCN8A | CNS/PNS | 6 | — | Pain, movement disorders |
| $Na_v1.7$ | SCN9A | PNS | 25 | Erythermalgia | Pain |
| $Na_v1.8$ | SCN10A | PNS | 50000 | — | Pain |
| $Na_v1.9$ | SCN11A | PNS | 1000 | — | Pain |

There are currently 10 known members of the family of voltage-gated sodium channel (VGSC) alpha subunits. Names for this family include SCNx, SCNAx, and $Na_vx.x$. The VGSC family has been phylogenetically divided into two subfamilies $Na_v1.x$ (all but SCN6A) and $Na_v2.x$ (SCN6A). The Nav1.x subfamily can be functionally subdivided into two groups, those which are sensitive to blocking by tetrodotoxin (TTX-sensitive or TTX-s) and those which are resistant to blocking by tetrodotoxin (TTX-resistant or TTX-r).

There are three members of the subgroup of TTX-resistant sodium channels. The SCN5A gene product ($Na_v1.5$, H1) is almost exclusively expressed in cardiac tissue and has been shown to underlie a variety of cardiac arrhythmias and conduction disorders (Liu H, et al., *Am J Pharmacogenomics.* 2003; 3(3):173-9). Consequently, blockers of Nav1.5 have found clinical utility in treatment of such disorders (Srivatsa U, et al., *Curr Cardiol Rep.* 2002 September; 4(5):401-10).

tal lethality (Planells-Cases R et al., *Biophys J.* 2000 June; 78(6):2878-91). Expression of the Nav1.4 gene is largely restricted to skeletal muscle and, accordingly, mutations of this gene are associated with a variety of movement disorders (Ptacek, L. J., *Am. J. Hum. Genet.* 49: 851-854, 1991; Hudson A J, *Brain.* 1995 April; 118 (Pt 2):547-63). The majority of these disorders are related to hyperactivity or "gain-of-function" and have been found to respond to treatment with sodium channel blockers (Desaphy J F, et al., *J Physiol.* 2004 Jan. 15; 554(Pt 2):321-34).

Neither the SCN3A nor the SCN8A VGSC genes have been conclusively linked to heritable disorders in humans. Loss-of-function mutations of the SCN8A gene are known in mice and yield increasingly debilitating phenotypes, dependent upon the remaining functionality of the gene products (Meisler M H, *Genetica.* 2004 September; 122(1):37-45). Homozygous null mutations cause progressive motor neuron failure leading to paralysis and death, while heterozygous null animals are asymptomatic. Homozygous med$^J$ mice have nearly 90% reduction in functional Nav1.6 current and exhibit dystonia and muscle weakness but are still viable. Evidence for Nav1.6 being important for nociception is largely associative as Nav1.6 is expressed at high levels in dorsal root ganglia and can be found in spinal sensory tracts (Tzoumaka E, *J Neurosci Res.* 2000 Apr. 1; 60(1):37-44). It should be noted however that expression of Nav1.6 is not restricted to sensory neurons of the periphery. Like the Nav1.6 channel, expression of the Nav1.3 VGSC can also be detected in both the central and peripheral nervous system, though levels in the adult CNS are generally much higher than PNS. During development and the early postnatal period Nav1.3 is expressed in peripheral neurons but this expression wanes as the animal matures (Shah B S, *Physiol.* 2001 Aug. 1; 534(Pt 3):763-76; Schaller K L, *Cerebellum.* 2003; 2(1):2-9). Following neuronal insult Nav1.3 expression is upregulated, more closely mimicking the developmental expression patterns (Hains B C, *J Neurosci.* 2003 Oct. 1; 23(26):8881-92). Coincident with the recurrence of Nav1.3 expression is the emergence of a rapidly re-priming sodium current in the injured axons with a biophysical profile similar to Nav1.3 (Leffler A, et al., *J Neurophysiol.* 2002 August; 88(2):650-8). Treatment of injured axons with high levels of GDNF has been shown to diminish the rapidly repriming sodium current and reverses thermal and mechanical pain-related behaviors in a rat model of nerve injury, presumably by down-regulating the expression of Nav1.3 (Boucher T J, *Curr Opin Pharmacol.* 2001 February; 1(1):66-72). Specific down-regulation of Nav1.3 via treatment with antisense oligonucleotides has also been shown to reverse pain-related behaviors following spinal cord injury (Hains B C, *J Neurosci.* 2003 Oct. 1; 23(26): 8881-92).

The Na$_v$1.7 (PN1, SCN9A) VGSC is sensitive to blocking by tetrodotoxin and is preferentially expressed in peripheral sympathetic and sensory neurons. The SCN9A gene has been cloned from a number of species, including human, rat, and rabbit and shows ~90% amino acid identity between the human and rat genes (Toledo-Aral et al., *Proc Natl Acad Sci USA.* 1997 Feb. 18; 94(4): 1527-1532).

An increasing body of evidence suggests that Na$_v$1.7 may play a key role in various pain states, including acute, inflammatory and/or neuropathic pain. Deletion of the SCN9A gene in nociceptive neurons of mice led to a reduction in mechanical and thermal pain thresholds and reduction or abolition of inflammatory pain responses (Nassar et al., *Proc Natl Acad Sci USA.* 2004 Aug. 24; 101(34):12706-11). In humans, Na$_v$1.7 protein has been shown to accumulate in neuromas, particularly painful neuromas (Kretschmer et al., *Acta Neurochir (Wien).* 2002 August; 144(8):803-10). Mutations of Na$_v$1.7, both familial and sporadic, have also been linked to primary erythermalgia, a disease characterized by burning pain and inflammation of the extremities (Yang et al., *J Med Genet.* 2004 March; 41(3):171-4). Congruent with this observation is the report that the non-selective sodium channel blockers lidocaine and mexiletine can provide symptomatic relief in cases of familial erythermalgia (Legroux-Crepel et al., *Ann Dermatol Venereol* 130:429-433).

Sodium channel-blocking agents have been reported to be effective in the treatment of various disease states, and have found particular use as local anesthetics and in the treatment of cardiac arrhythmias. It has also been reported that sodium channel-blocking agents may be useful in the treatment of pain, including acute, chronic, inflammatory and/or neuropathic pain; see, for example, Wood, J N et al., *J Neurobiol.* 2004 October; 61(1):55-71. Preclinical evidence demonstrates that sodium channel-blocking agents can suppress neuronal firing in peripheral and central sensory neurons, and it is via this mechanism that they may be useful for relieving pain. In some instances abnormal or ectopic firing can originate from injured or otherwise sensitized neurons. For example, it has been shown that sodium channels can accumulate in peripheral nerves at sites of axonal injury and may function as generators of ectopic firing (Devor et al. *J. Neurosci.* 132: 1976 (1993)). Changes in sodium channel expression and excitability have also been shown in animal models of inflammatory pain where treatment with proinflammatory materials (CFA, Carrageenan) promoted pain-related behaviors and correlated with increased expression of sodium channel subunits (Gould et al., *Brain Res.* 1999 Apr. 10; 824(2): 296-9; Black et al., *Pain.* 2004 April; 108(3):237-47). Alterations in either the level of expression or distribution of sodium channels, therefore, may have a major influence on neuronal excitability and pain-related behaviors.

Many patients with either acute or chronic pain disorders respond poorly to current pain therapies and resistance or insensitivity to opiates is common. In addition, many of the currently available treatments have undesirable side effects. It has been reported that there is no treatment to prevent the development of neuropathic pain or to control established neuropathic pain. Mannion et al., *Lancet,* 353: 1959-1964 (1999).

Ohkawa et al. have described a class of cyclic ethers that are of use as sodium channel blockers (U.S. Pat. No. 6,172, 085).

Currently, gabapentin is the principal treatment for neuropathic pain. As with epilepsy, its mechanism of action for pain is unknown. However, as little as only 30% of patients respond to gabapentin treatment for neuropathic pain.

In view of the limited number of agents presently available and the low levels of efficacy of the available agents, there is a pressing need for compounds that are potent, specific inhibitors of ion channels implicated in neuropathic pain. The present invention provides such compounds, methods of using them, and compositions that include the compounds.

SUMMARY OF THE INVENTION

It has now been discovered that various heterocyclic aryl sulfonamides are potent modulators of sodium channels. In the discussion that follows, the invention is exemplified by reference to the inhibition of sodium channels that are localized in the peripheral nervous system, and in particular those compounds that are selective inhibitors of TTX-s sodium channels, and are useful for treating pain through the inhibition of sodium ion flux through channels that include a TTX-s sodium channel subunit. The compounds and methods of the present invention are useful for treating diseases in which modulating one or more TTX-s sodium channels provides relief from the disease. Of particular interest is the use of the compounds and methods of the invention for treating pain and central or peripheral nervous system disorders, preferably peripheral nervous system disorders. The present invention is of use for treating acute, chronic, inflammatory, and/or neuropathic pain.

The present invention provides compounds that are useful in the treatment of diseases through the modulation of sodium ion flux through voltage-dependent sodium channels. More particularly, the invention provides compounds, compositions and methods that are useful in ameliorating or alleviating conditions susceptible to such ion channel modulation as more fully described below.

In a first aspect, the invention provides a compound according to Formula I:

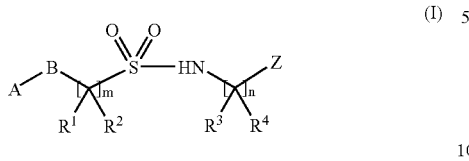

In this formula, $R^1$, $R^2$, $R^3$ and $R^4$ can be members independently selected from H, F, $CF_3$, substituted or unsubstituted $C_1$-$C_4$ alkyl, unsubstituted 3- to 7-membered cycloalkyl and unsubstituted 3- to 7-membered heterocycloalkyl.

The symbol A represents a member selected from:

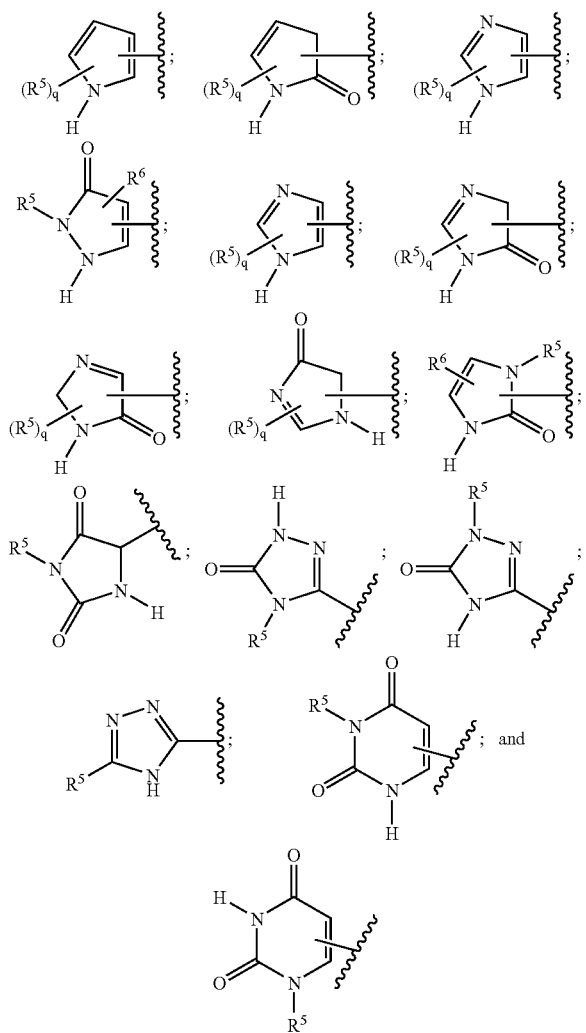

$R^5$ can be a member selected from $C_1$-$C_4$ substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. The index q represents a member selected from the integers from 0 to 2. $R^6$ can be a member selected from H, halogen, $CF_3$, $C_1$-$C_4$ substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl.

The symbol B represents a member selected from:

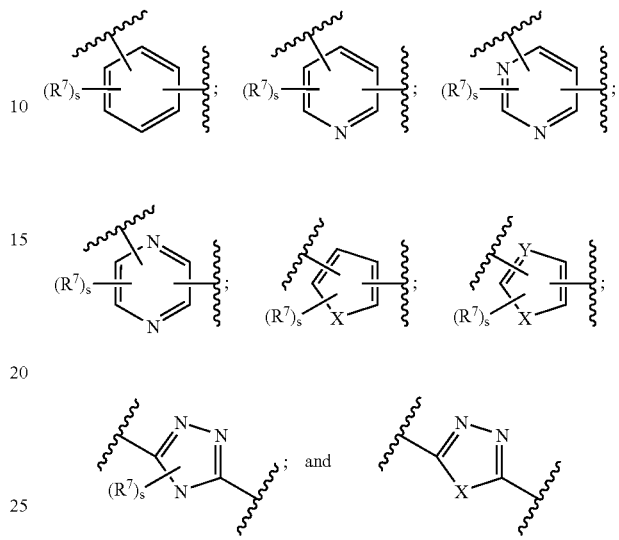

The symbol X represents a member selected from O and S.

The symbol Y represents a member selected from CH and N. The index s represents an integer greater than 0, sufficient to satisfy the valence requirements of the ring atoms. Each $R^7$ can be a member independently selected from H, $OR^8$, $NR^9R^{10}$, $SO_2NR^9R^{10}$, cyano, halogen, $CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^8$ can be a member selected from H, $CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^9$ and $R^{10}$ can be members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl.

The symbol Z can be a member selected from:

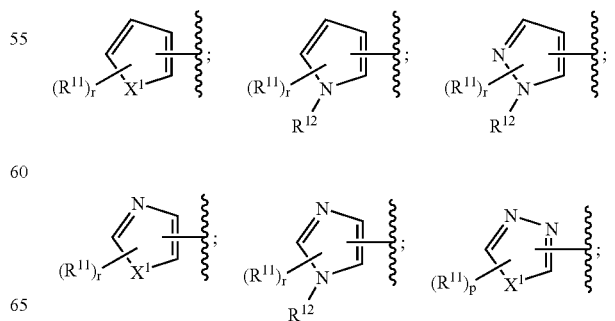

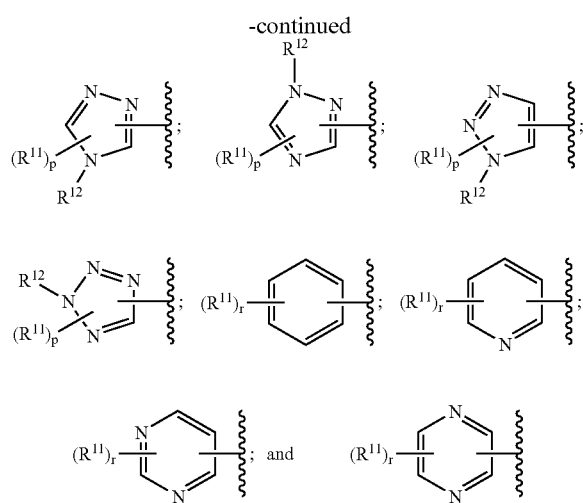

Each $R^{11}$ can be a member independently selected from H, $OR^{13}$, $NR^{14}R^{15}$, $SO_2NR^{14}R^{15}$, cyano, halogen, $CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^{13}$ can be a member selected from H, $CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^{14}$ and $R^{15}$ can be members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^{14}$ and $R^{15}$, together with the nitrogen to which they can be bound, can be optionally joined to form a substituted or unsubstituted 5- to 7-membered ring. The index r represents a member selected from the integers from 0 to 2. The index p represents a member selected from the integers from 0 to 1. $R^{12}$ can be a member selected from $C_1$-$C_4$ substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. The indices m and n can independently represent an integer selected from 0 to 2, such that when a member selected from m and n can be greater than 1, each $R^1$ and $R^2$; $R^3$ and $R^4$, respectively, can be independently selected.

In another aspect, the present invention provides pharmaceutical compositions comprising a pharmaceutically acceptable excipient and a compound as provided above.

In yet another aspect, the present invention provides a method for modulating the activity of a sodium channel is a subject, comprising administering to a subject an amount of a compound as provided above which is sufficient to modulate the activity.

In still another aspect, the present invention provides a method of ameliorating or alleviating a condition in a subject. The condition can be a member selected from pain, irritable bowel syndrome, Crohn's disease, epilepsy, seizures multiple sclerosis, bipolar depression and tachy-arrhythmias. The method comprises administering to the subject an amount of a compound of the invention sufficient to ameliorate or alleviate said condition.

Additional aspects, advantages and objects of the present invention will be apparent from the detailed description that follows.

BRIEF DESCRIPTION OF THE DRAWINGS

FIG. 1 provides a representative list of the compounds of the invention.

DETAILED DESCRIPTION OF THE INVENTION

Abbreviations

The abbreviations used herein generally have their conventional meaning within the chemical and biological arts. For example: CHO, Chinese hamster ovary; EBSS, Earl's Balanced Salt Solution; SDS, sodium dodecyl sulfate; $Et_3N$, triethylamine; MeOH, methanol; and DMSO, dimethylsulfoxide.

DEFINITIONS

The term "pain" refers to all categories of pain, including pain that is described in terms of stimulus or nerve response, e.g., somatic pain (normal nerve response to a noxious stimulus) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic neuropathy (see, e.g., Harrison's Principles of Internal Medicine, pp. 93-98 (Wilson et al., eds., 12th ed. 1991); Williams et al., J. of Medicinal Chem. 42:1481-1485 (1999), herein each incorporated by reference in their entirety).

"Somatic" pain, as described above, refers to a normal nerve response to a noxious stimulus such as injury or illness, e.g., trauma, burn, infection, inflammation, or disease process such as cancer, and includes both cutaneous pain (e.g., skin, muscle or joint derived) and visceral pain (e.g., organ derived).

"Neuropathic" pain, as described above, refers to pain resulting from injury to or chronic changes in peripheral and/or central sensory pathways, where the pain often occurs or persists without an obvious noxious input.

"Acute pain", as described above, refers to pain which is marked by short duration or a sudden onset.

"Chronic pain", as described above, refers to pain which is marked by long duration or frequent recurrence.

"Inflammatory pain", as described above, refers to pain which is produced as a symptom or a result of inflammation or an immune system disorder.

"Visceral pain", as described above, refers to pain which is located in an internal organ.

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

"Compound of the invention," as used herein refers to the compounds discussed herein, pharmaceutically acceptable salts and prodrugs of these compounds.

"Inhibiting" and "blocking," are used interchangeably herein to refer to the partial or full blockade of a voltage sodium gated channel by a compound of the invention, which leads to a decrease in ion flux either into or out of a cell in which a voltage sodium gated channel is found.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N and S, and wherein the nitrogen and sulfur atoms may optionally be oxidized and the nitrogen heteroatom may optionally be quaternized. The heteroatom(s) O, N and S may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R''' and R'''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''' and R'''' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R''' and R'''' groups when more than one of these groups is present.

Two of the substituents on adjacent atoms of the aryl or heteroaryl ring may optionally be replaced with a substituent of the formula —T—C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula —A—(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$)alkyl.

As used herein, the term "heteroatom" includes oxygen (O), nitrogen (N) and sulfur (S).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, and substituted or unsubstituted heterocyclyl groups.

The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Description of the Embodiments

I. The Compounds

In a first aspect, the invention provides a compound according to Formula I:

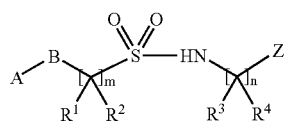

(I)

In this formula, $R^1$, $R^2$, $R^3$ and $R^4$ can be members independently selected from H, F, $CF_3$, substituted or unsubstituted $C_1$-$C_4$ alkyl, unsubstituted 4- to 7-membered cycloalkyl and unsubstituted 4- to 7-membered heterocycloalkyl.

The symbol A represents a member selected from:

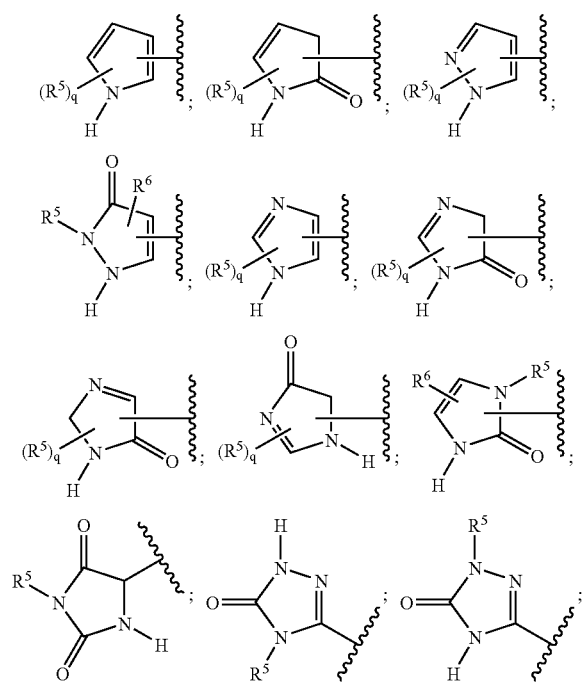

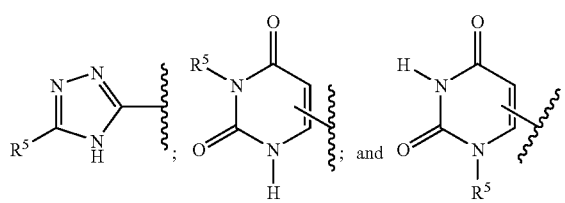

$R^5$ can be a member selected from $C_1$-$C_4$ substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. The index q represents a member selected from the integers from 0 to 2. $R^6$ can be a member selected from H, halogen, $CF_3$, $C_1$-$C_4$ substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl.

The symbol B represents a member selected from:

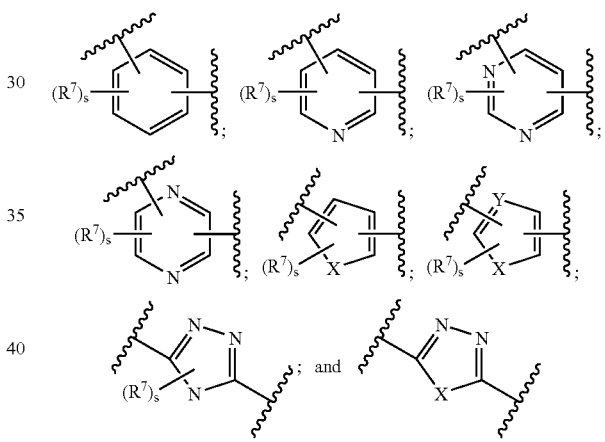

The symbol X represents a member selected from O and S.

The symbol Y represents a member selected from CH and N. The index s represents an integer greater than 0, sufficient to satisfy the valence requirements of the ring atoms. Each $R^7$ can be a member independently selected from H, $OR^8$, $NR^9R^{10}$, $SO_2NR^9R^{10}$, cyano, halogen, $CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^8$ can be a member selected from H, $CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^9$ and $R^{10}$ can be members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl.

The symbol Z can be a member selected from:

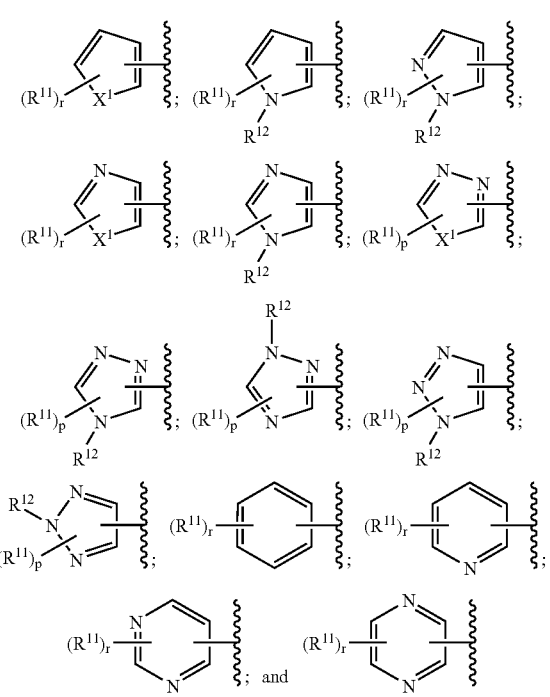

Each $R^{11}$ can be a member independently selected from H, $OR^{13}$, $NR^{14}R^{15}$, $SO_2NR^{14}R^{15}$, cyano, halogen, $CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^{13}$ can be a member selected from H, $CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^{14}$ and $R^{15}$ can be members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^{14}$ and $R^{15}$, together with the nitrogen to which they can be bound, can be optionally joined to form a substituted or unsubstituted 5- to 7-membered ring. The index r represents a member selected from the integers from 0 to 2. The index p represents a member selected from the integers from 0 to 1. $R^{12}$ can be a member selected from $C_1$-$C_4$ substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. The indices m and n can independently represent an integer selected from 0 to 2, such that when a member selected from m and n can be greater than 1, each $R^1$ and $R^2$; $R^3$ and $R^4$, respectively, can be independently selected.

In an exemplary embodiment, the indices m and n can be 0. In another exemplary embodiment, the symbol A can be a member selected from:

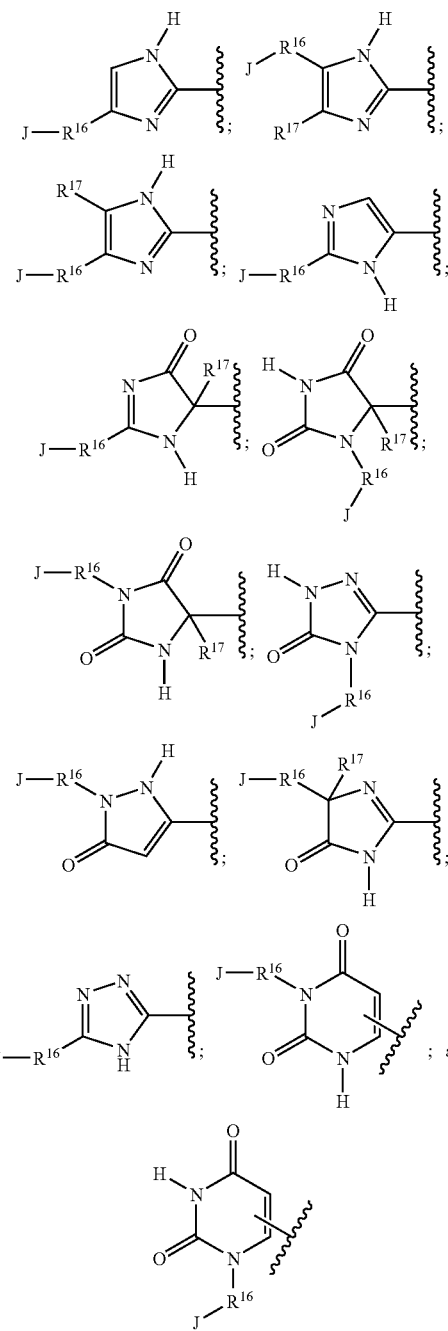

The symbol J can be a member selected from substituted or unsubstituted aryl and substituted or unsubstituted heteroaryl. $R^{16}$ can be a member selected from a bond, —O—, —S—, substituted or unsubstituted alkylene, substituted or unsubstituted cycloalkylene, substituted or unsubstituted heterocycloalkylene, substituted or unsubstituted heteroalkylene, substituted or unsubstituted arylene and substituted or unsubstituted heteroarylene; and $R^{17}$ can be a member selected from H, halogen, $CF_3$, substituted or unsubstituted $C_1$-$C_4$ alkyl, an unsubstituted 4- to 7-membered cycloalkyl ring and an unsubstituted 4- to 7-membered heterocycloalkyl ring.

In another exemplary embodiment, J-$R^{16}$ has the formula:

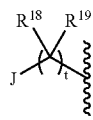

$R^{18}$ and $R^{19}$ can be members independently selected from H, substituted or unsubstituted alkyl, substituted or unsubstituted heteroalkyl, and substituted or unsubstituted aryl. $R^{18}$ and $R^{19}$, together with the carbon to which they can be attached, can be optionally joined to form a member selected from a substituted or unsubstituted 3- to 7-member cycloalkyl moiety and substituted or unsubstituted 5- to 7-member heterocycloalkyl moiety; and t can be an integer selected from 0 to 4, such that when t can be greater than 1, each $R^{18}$ and $R^{19}$ can be independently selected.

In another exemplary embodiment, the compound has the formula:

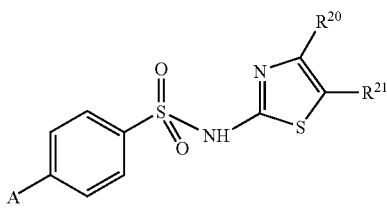

$R^{20}$ and $R^{21}$ can be members independently selected from can be a member independently selected from H, $OR^{22}$, $NR^{23}R^{24}$, $SO_2NR^{23}R^{24}$, cyano, halogen, $CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^{22}$ can be a member selected from H, $CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^{23}$ and $R^{24}$ can be members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^{23}$ and $R^{24}$, together with the nitrogen to which they can be bound, can be optionally joined to form a substituted or unsubstituted 5- to 7-membered ring. In another exemplary embodiment, the compound has inhibitory activity against a voltage-gated sodium channel.

In a second aspect, the invention provides a pharmaceutical formulation comprising a compound according to Formula I.

In a third aspect, the invention provides a method of modulating the activity of a sodium channel in a subject. This method comprises administering to a subject an amount of the compound according to Formula I sufficient to modulate said activity.

In a fourth aspect, the invention provides a method of ameliorating or alleviating a condition in a subject. The condition can be a member selected from pain, irritable bowel syndrome, Crohn's disease, epilepsy, seizures multiple sclerosis, bipolar depression and tachy-arrhythmias. The method includes administering to the subject an amount of the compound of the invention sufficient to ameliorate or alleviate the condition. In an exemplary embodiment, the condition is pain, and the pain can be a member selected from acute pain, chronic pain, visceral pain, inflammatory pain and neuropathic pain.

Representative compounds according to Formula I are set forth in FIG. 1.

Also within the scope of the present invention are compounds of the invention that are poly- or multi-valent species, including, for example, species such as dimers, trimers, tetramers and higher homologs of the compounds of the invention or reactive analogues thereof. The poly- and multi-valent species can be assembled from a single species or more than one species of the invention. For example, a dimeric construct can be "homo-dimeric" or "heterodimeric." Moreover, poly- and multi-valent constructs in which a compound of the invention or a reactive analogue thereof, can be attached to an oligomeric or polymeric framework (e.g., polylysine, dextran, hydroxyethyl starch and the like) are within the scope of the present invention. The framework is preferably polyfunctional (i.e. having an array of reactive sites for attaching compounds of the invention). Moreover, the framework can be derivatized with a single species of the invention or more than one species of the invention.

Moreover, the present invention includes compounds within the motif set forth in Formula I, which are functionalized to afford compounds having water-solubility that is enhanced relative to analogous compounds that are not similarly functionalized. Thus, any of the substituents set forth herein can be replaced with analogous radicals that have enhanced water solubility. For example, it is within the scope of the invention to, for example, replace a hydroxyl group with a diol, or an amine with a quaternary amine, hydroxy amine or similar more water-soluble moiety. In a preferred embodiment, additional water solubility is imparted by substitution at a site not essential for the activity towards the ion channel of the compounds set forth herein with a moiety that enhances the water solubility of the parent compounds. Methods of enhancing the water-solubility of organic compounds are known in the art. Such methods include, but are not limited to, functionalizing an organic nucleus with a permanently charged moiety, e.g., quaternary ammonium, or a group that is charged at a physiologically relevant pH, e.g. carboxylic acid, amine. Other methods include, appending to the organic nucleus hydroxyl- or amine-containing groups, e.g. alcohols, polyols, polyethers, and the like. Representative examples include, but are not limited to, polylysine, polyethyleneimine, poly(ethyleneglycol) and poly(propyleneglycol). Suitable functionalization chemistries and strategies for these compounds are known in the art. See, for example, Dunn, R. L., et al., Eds. POLYMERIC DRUGS AND DRUG DELIVERY SYSTEMS, ACS Symposium Series Vol. 469, American Chemical Society, Washington, D.C. 1991.

II. Preparation of the Compounds

Compounds of the present invention can be prepared using readily available starting materials or known intermediates. The synthetic schemes set forth below provide exemplary synthetic pathways for the preparation of compounds of the invention.

II.a. General Procedure for Synthesizing Imidazole-Containing Compounds

Imidazole-containing compounds of the invention can be synthesized by the following scheme.

Imidazole-containing compounds can also be synthesized by the following scheme.

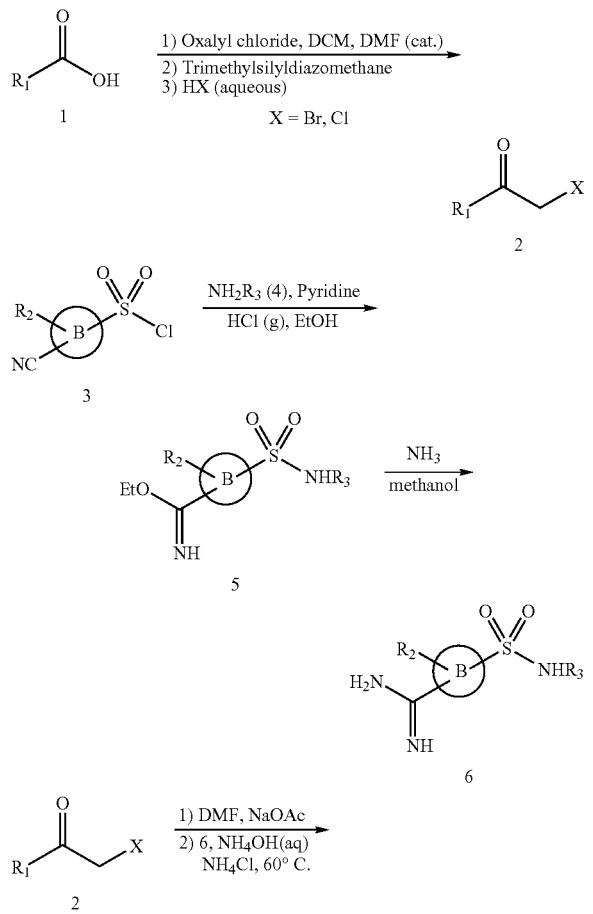

A typical procedure for the synthesis of 10 involves the formation of a sulfonamide of 8 with an amine 4 in the presence of a base such as pyridine followed by the condensation and cyclization of the aldehyde and a diketo derivative 9 in an ammonium solution at an elevated temperature such as 80° C.

II.b. General Procedure for Synthesizing Triazole-Containing Compounds

Triazole-containing compounds of the invention can be synthesized by the following scheme.

A typical procedure for the synthesis of 7 involves the reaction of the appropriately substituted 2-bromoketone 2 with the amidine derivative 6 in a polar solvent such as DMF in the presence of NaOAc, NH$_4$OH, NH$_4$Cl at an elevated temperature such as 60° C.

The substituted 2-bromoketone 2 can be prepared by the reaction of a substituted benzoic acyl chloride with trimethylsilydiazomethane followed by bromination with concentrated hydrobromic acid. The substituted benzoic acyl chloride derivatives can be obtained either from the reaction of a substituted acyl acid 1 and oxalyl chloride in the presence of catalytical amount DMF in chloromethane or from commercially available sources.

The substituted 6 can be synthesized in two steps. Starting from a substituted sulfonyl chloride 3, the intermediate 5 can be obtained by reacting 3 with an appropriate amine 4 in a base such as pyridine followed by acid hydrolysis of the resulting nitrile derivative. The intermediate 5 then can be converted to amidine 6 using an ammonia solution in an organic solvent such as methanol.

A typical procedure for the synthesis of 13 involves the reaction of the appropriate acyl chloride 12 with an amino amidine derivative 11 in the presence of a base such as triethyl amine followed by the cyclization of the acyl aminoamidine in an acidic environment at an elevated temperature such as 60° C.

The substituted amino amidine 11 can be obtained from the reaction of a substituted imidate with hydrazine in an organic solvent such as ethanol.

Intermediate 5 can be synthesized as described in the Example 1.

Triazole-containing compounds of the invention can also be synthesized by the following scheme.

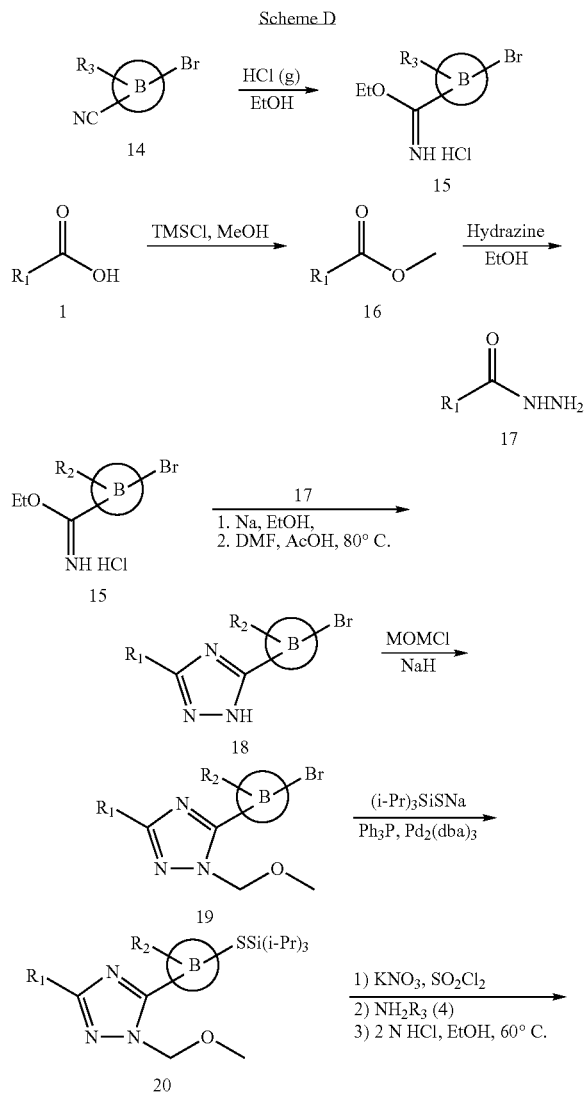

This process requires three steps starting from 20. The silyl thiol 20 can first be converted to its corresponding sulfonyl chloride by potassium nitrate and sulfuryl chloride and the chloride can later be quenched with an amine. The deprotection of the methoxyl methyl group with an acid in an organic solvent such as ethanol yields the desired product 13. The silyl thiol 20 can be prepared by palladium catalyzed coupling reaction between a bromo aryl derivative 19 and sodium silyl thioxide. Reacting a hydrazide derivative 17 with a substituted imidic acid ester 15, followed by the cyclization and the protection of the triazole derivative, can produce the bromo aryl derivative 18.

The intermediate 15 can be prepared through acid hydrolysis of a nitrile derivative 14 and the intermediate 17 can be obtained from an ester 16 of the acid 1.

Triazole-containing compounds of the invention can also be synthesized by the following scheme.

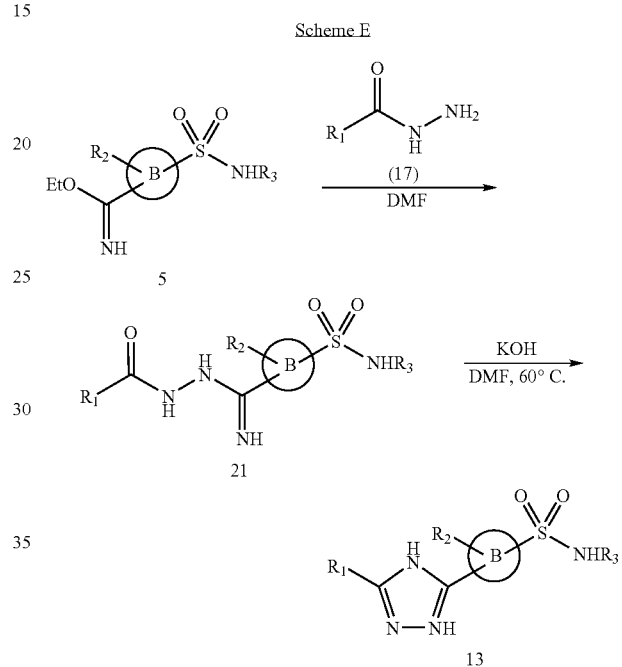

An alternative synthesis of the triazoles 13 involves reacting a benzimidic acid ethyl ester 5 with a hydrazide 17 followed by the cyclization of the crude intermediate 21 under basic conditions, such as those involving potassium hydroxide.

II.c. General Procedure for Synthesizing Benzimidazole-Containing Compounds

Benzimidazole-containing compounds of the invention can be synthesized by the following scheme.

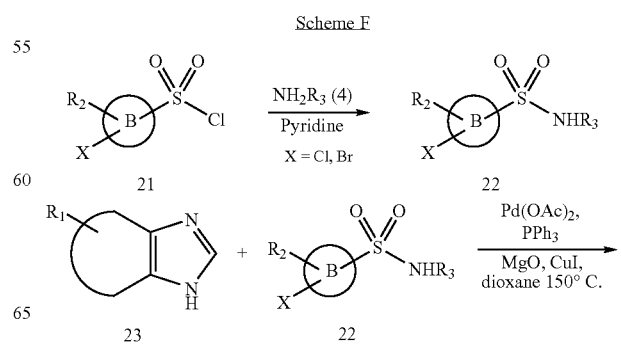

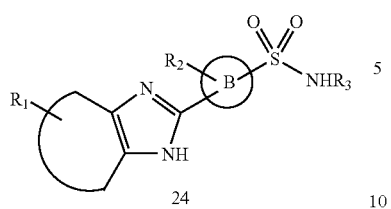

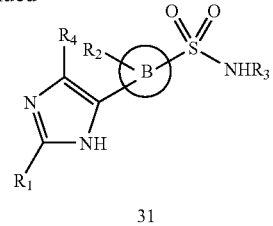

A typical procedure for the synthesis of benzimidazole 24 involves reacting a halo benzenesulfonamide 22 with benzimidazole 23 to form the desired benzimidazole 24 using a palladium coupling reaction.

II.d. General Procedure for Synthesizing Isoimidazole-Containing Compounds

Isoimidazole-containing compounds of the invention can be synthesized by the following scheme.

A typical procedure for the synthesis of 31 involves the reaction of the appropriately substituted 2-bromoketone 28 with the amidine derivative 29 in a polar solvent such as DMF at an elevated temperature such as 60° C.

The substituted 2-bromoketone 28 can be prepared by the bromination of a substituted phenone 27 with reagents such as pyridinium tribromide. The substituted phenone 27 can be obtained in two steps from a commercially available substituted sulfonyl chloride 25 using the methods described in the preparation of Example 1.

II.e. General Procedure for Synthesizing Pyrazole-Containing Compounds

Pyrazole-containing compounds of the invention can be synthesized by the following scheme.

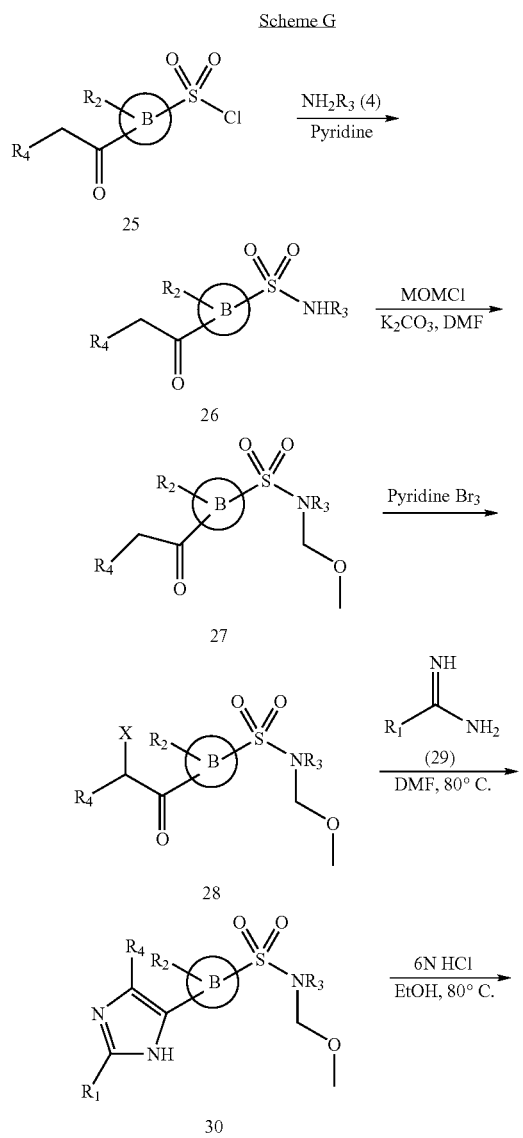

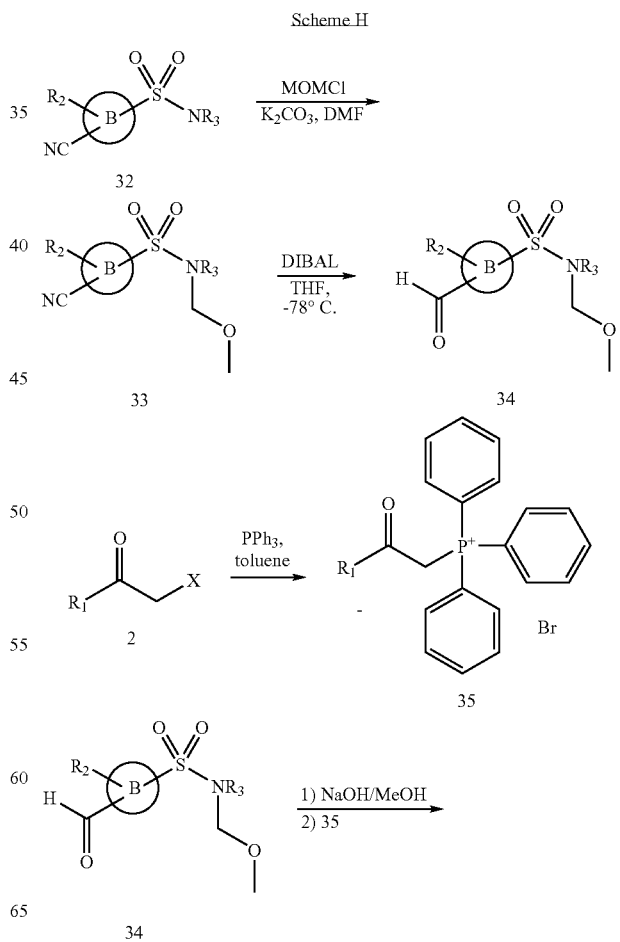

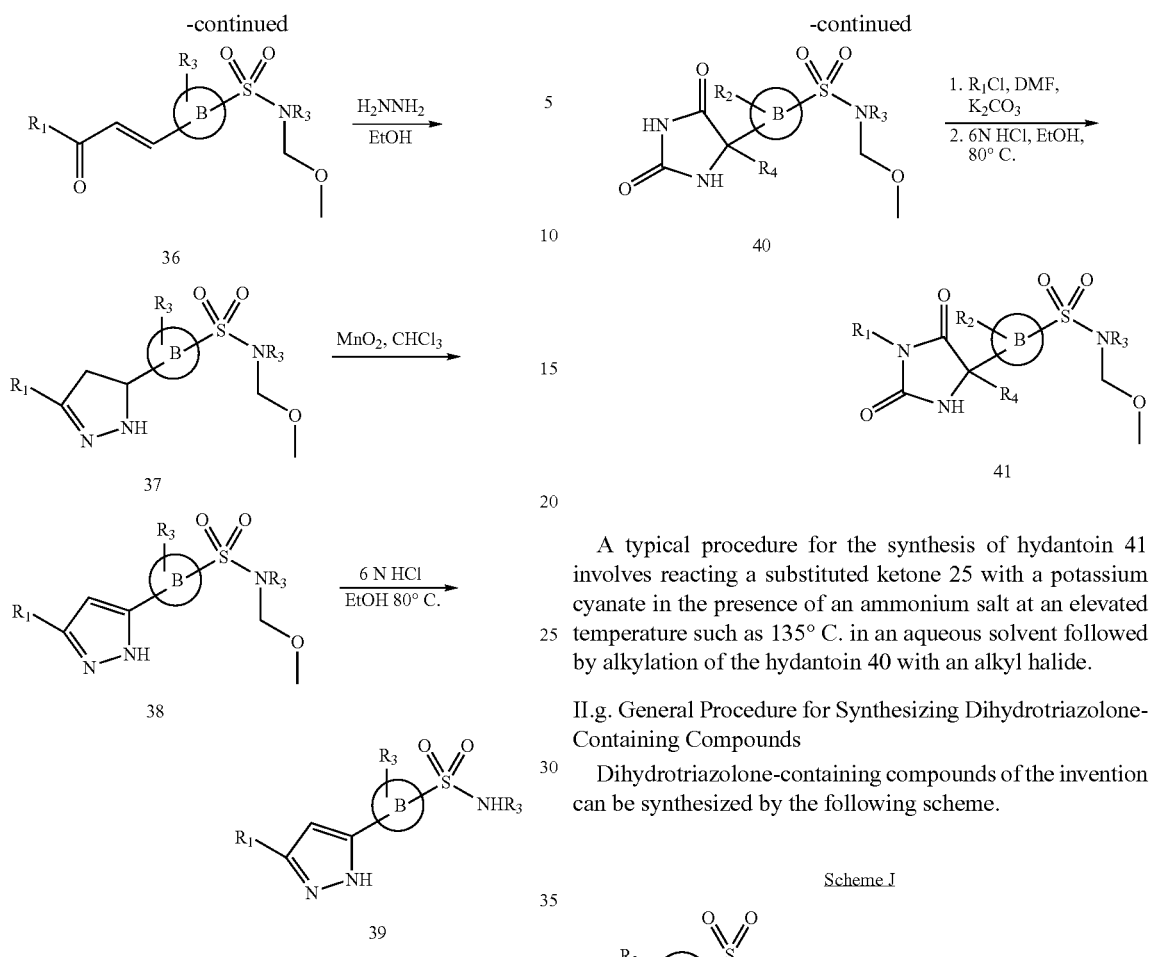

A typical procedure for the synthesis of 39 involves a Wittig reaction between phosphonium bromide 35 and aldehyde 34 to form enone 36. Phosphonium bromide 35 can be formed by the reaction of halo ketones with triphenylphosphine. The aldehyde 34 can be prepared by the reduction of a nitrile derivative 33. After enone 36 is formed it can be reacted with hydrazine to yield pyrazoline 37. The pyrazoline 37 can be oxidized to the pyrazole 38 with manganese oxide. The sulfonamide of 38 can be deprotected to yield the desired compound 39.

II.f General Procedure for Synthesizing Hydantoin-Containing Compounds

Hydantoin-containing compounds of the invention can be synthesized by the following scheme.

Scheme I

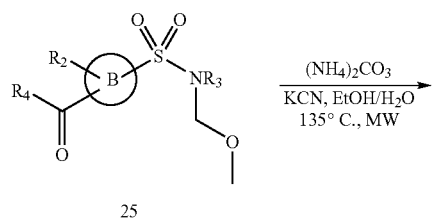

A typical procedure for the synthesis of hydantoin 41 involves reacting a substituted ketone 25 with a potassium cyanate in the presence of an ammonium salt at an elevated temperature such as 135° C. in an aqueous solvent followed by alkylation of the hydantoin 40 with an alkyl halide.

II.g. General Procedure for Synthesizing Dihydrotriazolone-Containing Compounds

Dihydrotriazolone-containing compounds of the invention can be synthesized by the following scheme.

Scheme J

A typical procedure for the synthesis of 44 involves the cyclization of 43 under basic conditions. 43 can be formed by first reacting isocyanate 42 with hydrazine to form a hydrazide urea. This hydrazide urea can then be added to imidate ester 5 to produce 43.

Dihydrotriazolone-containing compounds of the invention can also be synthesized by the following scheme.

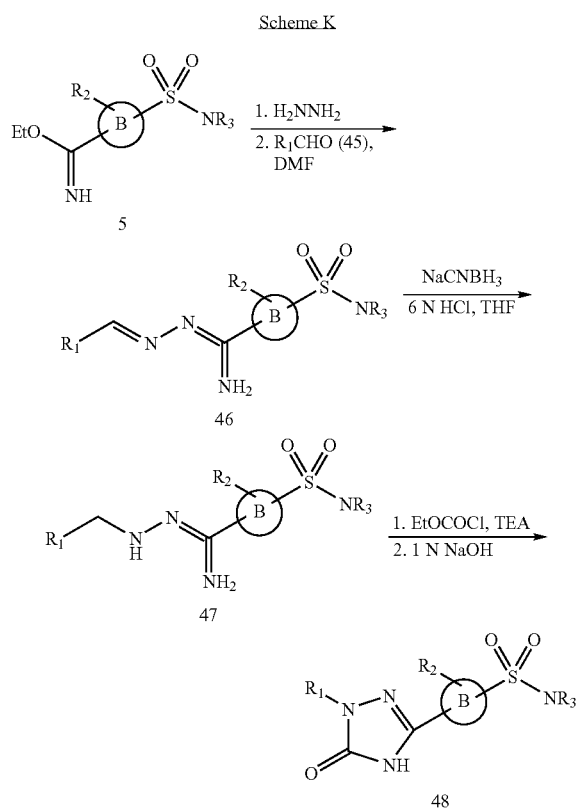

Scheme K

A typical procedure for the synthesis of 48 involves carbamation of 46 followed by basic cyclization. 46 can be formed by first reacting imidate ester 5 with hydrazine to form a amino amidine. This amino amidine can be then condensed with an aldehyde 45 to produce imine 46.

III. Assays for Blockers of Voltage-Dependent TTX-Sensitive Sodium Channels

The activity of sodium channels can be assessed using a variety of in vitro assays, including but not limited to, measuring ion flux, measuring transmembrane potential, and/or measuring ionic current. Measurement of ionic fluxes can be accomplished by measuring changes in the concentration of the permeant species or by tracking the movement of small amounts of an appropriately permeant radioactive tracer. Transmembrane potential can be assessed with voltage-sensitive fluorescent dyes or, more sensitively, with electrophysiological methods.

Determination of the effectiveness of compounds as ex vivo blockers of sodium channels can be assessed by the inhibition of compound action potential propagation in isolated nerve preparations (Kourtney and Stricharz, LOCAL ANESTHETICS, Springer-Verlag, New York, 1987). A number of experimental models in the rat are appropriate for assessing the in vivo efficacy of the compounds of the invention. For example, the neuropathic pain model produced by the tight ligation of spinal nerves, described by Kim et al., Pain 50: 355-363 (1992) can be used to experimentally determine the effect of the compounds of the invention in an in vivo model of pain. Mechanical sensitivity can also be assessed using a procedure described by Chaplan et al., J. Neurosci. Methods 53: 55-63 (1994). Other assays of use are known to those of skill in the art. See, for example, U.S. Pat. No. 6,262,078.

Modulators of TTX-sensitive sodium channels can be tested using biologically active recombinant channels, or naturally occurring TTX-sensitive sodium channels, or by using native cells, like neurons expressing a TTX-sensitive sodium current. TTX-sensitive sodium channels can be isolated, co-expressed or expressed in a cell, or expressed in a membrane derived from a cell. In such assays, TTX-sensitive sodium channels are generally expressed alone to form a homomeric sodium channel or may be co-expressed with a second subunit (e.g., an auxiliary beta subunit) so as to form a heteromeric sodium channel. The TTX-sensitive sodium channels are stably expressed in HEK-293 cells, an example of an effective mammalian expression system.

Modulation can be tested using one of the in vitro or in vivo assays described above. Samples or assays that are treated with a potential sodium channel inhibitor are compared to control samples without the test compound, to examine the extent of modulation. Control samples (untreated with inhibitors) are assigned a relative sodium channel activity value of 100. Inhibition of TTX-sensitive sodium channels is achieved when the sodium channel activity value relative to the control is less than 70%, preferably less than 40% and still more preferably, less than 30%. Compounds that decrease the flux of ions will cause a detectable decrease in the ion current density by decreasing the probability of a TTX-sensitive sodium channel being open, by decreasing conductance through the channel, decreasing the number of channels, or decreasing the expression of channels.

Changes in ion flux may be assessed by determining changes in polarization (i.e., electrical potential) of the cell or membrane expressing the sodium channel. A preferred means to determine changes in cellular polarization is by measuring changes in current or voltage with the voltage-clamp and patch-clamp techniques, using the "cell-attached" mode, the "inside-out" mode, the "outside-out" mode, the "perforated patch" mode, the "whole cell" mode or other means of controlling or measuring changes in transmembrane potential (see, e.g., Ackerman et al., New Engl. J. Med. 336: 1575-1595 (1997)). Whole cell currents are conveniently determined using the standard methodology (see, e.g., Hamill et al., Pflugers. Archiv. 391: 85 (1981). Other known assays include: radiotracer flux assays and fluorescence assays using voltage-sensitive dyes (see, e.g., Vestergarrd-Bogind et al., J. Membrane Biol. 88: 67-75 (1988); Daniel et al., J. Pharmacol. Meth. 25: 185-193 (1991); Holevinsky et al, J. Membrane Biology 137: 59-70 (1994)). Assays for compounds capable of inhibiting or increasing sodium flux through the channel proteins can be performed by application of the compounds to a bath solution in contact with and comprising cells having a channel of the present invention (see, e.g., Blatz et al., Nature 323: 718-720 (1986); Park, J. Physiol. 481: 555-570 (1994)). Generally, the compounds to be tested are present in the range from about 1 nM to about 100 mM, preferably from about 1 nM to about 30 µM. In an exemplary embodiment, the compounds to be tested are present in the range from about 1 nM to about 3 µM.

The effects of the test compounds upon the function of the channels can be measured by changes in the electrical currents or ionic flux or by the consequences of changes in currents and flux. Changes in electrical current or ionic flux are measured by either increases or decreases in flux of ions such as sodium or guanidinium ions (see U.S. Pat. No. 5,688, 830). The cations can be measured in a variety of standard ways. They can be measured directly by concentration changes of the ions or indirectly by membrane potential or by using radioactive ions. Consequences of the test compound on ion flux can be quite varied. Accordingly, any suitable physiological change can be used to assess the influence of a test compound on the channels of this invention. The effects of a test compound can be measured by a toxin-binding assay. When the functional consequences are determined using intact cells or animals, one can also measure a variety of effects such as transmitter release, hormone release, transcriptional changes to both known and uncharacterized genetic markers, changes in cell metabolism such as cell growth or pH changes, and changes in intracellular second messengers such as $Ca^{2+}$, or cyclic nucleotides.

High throughput screening (HTS) is of use in identifying promising candidate compounds of the invention. Physiologically, sodium channels open and close on a millisecond timescale. To overcome the short time in which channels are open the HTS assay can be run in the presence of an agent that modifies the gating of the channel, (e.g., pyrethroids, alpha-scorpion toxins, beta-scorpion toxins, batrachotoxin, etc). These agents modify the gating of sodium channels and keep the pore open for extended periods of time. In addition, while sodium channels are primarily selective for sodium, other ionic species can permeate the channel.

The specificity and effect of the TTX-sensitive sodium channel blocking agents of the invention can also be assayed against non-specific blockers of sodium channels, such as tetracaine, mexilitine, and flecainide.

IV. Pharmaceutical Compositions of VGSC Inhibitors

In another aspect, the present invention provides pharmaceutical compositions comprising a pharmaceutically acceptable excipient and a compound of Formula I provided above.

Formulation of the Compounds (Compositions)

The compounds of the present invention can be prepared and administered in a wide variety of oral, parenteral and topical dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermnally. Accordingly, the present invention also provides pharmaceutical compositions comprising a pharmaceutically acceptable carrier or excipient and either a compound of Formula I, or a pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

V. Methods for Inhibiting Ion Flow in VGSC

In yet another aspect, the present invention provides methods for decreasing ion flow through voltage gated sodium channels in a cell, comprising contacting a cell containing the target ion channels with a sodium channel-inhibiting amount of a compound of Formula I provided above.

The methods provided in this aspect of the invention are useful for the diagnosis of conditions that can be treated by inhibiting ion flux through voltage gated sodium channels, or for determining if a patient will be responsive to therapeutic agents, which act by inhibiting sodium channels.

VI. Methods for Treating Conditions Mediated by VGSC

In still another aspect, the present invention provides a method for the treatment of a disorder or condition through inhibition of a voltage gated sodium channel. In this method, a subject in need of such treatment is administered an effective amount of a compound having the formula provided above. In a preferred embodiment, the compounds provided herein are used to treat a disorder or condition by inhibiting an ion channel of the VGSC family, e.g., PN3.

The compounds provided herein are useful as sodium channel inhibitors and find therapeutic utility via inhibition of VGSCs in the treatment of diseases or conditions. The sodium channels that are typically inhibited are described herein as VGSCs such as the PN3 sodium channels.

The compounds of the invention are particularly preferred for use in the treating, preventing or ameliorating pain or seizures. The method includes administering to a patient in need of such treatment, a therapeutically effective amount of a compound according to Formula I, or a pharmaceutically acceptable salt thereof.

The compounds, compositions and methods of the present invention are of particular use in treating pain, including both inflammatory and neuropathic pain. Exemplary forms of pain treated by a compound of the invention include, postoperative pain, osteoarthritis pain, pain associated with metastatic cancer, neuropathy secondary to metastatic inflammation, trigeminal neuralgia, glossopharangyl neuralgia, adiposis dolorosa, burn pain, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, pain following stroke, thalamic lesions, radiculopathy, and other forms of neuralgic, neuropathic, and idiopathic pain syndromes.

Idiopathic pain is pain of unknown origin, for example, phantom limb pain. Neuropathic pain is generally caused by injury or infection of the peripheral sensory nerves. It includes, but is not limited to pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies.

Moreover, any VGSC inhibitory substance possessed of satisfactory VGSC modulating activity coupled with favorable intracranial transfer kinetics and metabolic stability is expected to show efficacy in central nervous system (CNS) diseases and disorders such as central nervous system ischemia, central nervous system trauma (e.g. brain trauma, spinal cord injury, whiplash injury, etc.), epilepsy, seizures, neurodegenerative diseases (e.g. amyotrophic lateral sclerosis (ALS), Alzheimer's disease, Huntington's chorea, Parkinson's disease, diabetic neuropathy, etc.), vascular dementia (e.g. multi-infarct dementia, Binswanger's disease, etc.), manic-depressive psychosis, depression, schizophrenia, chronic pain, trigeminal neuralgia, migraine, ataxia, bipolar disorder, spasticity, mood disorders, psychotic disorders, hearing and vision loss, age-related memory loss, learning deficiencies, anxiety and cerebral edema.

In treatment of the above conditions, the compounds utilized in the method of the invention are administered at the initial dosage of about 0.001 mg/kg to about 1000 mg/kg daily. A daily dose range of about 0.1 mg/kg to about 100 mg/kg is more typical. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages, which are less than the optimum dose of the compound. Thereafter, the dosage is increased by small increments until the optimum effect under the circumstances is reached. For convenience, the total daily dosage may be divided and administered in portions during the day, if desired.

EXAMPLES

The following examples are offered to illustrate, but not to limit the claimed invention. In the examples below, unless otherwise stated, temperatures are given in degrees Celsius ° C.); operations were carried out at room or ambient temperature (typically a range of from about 18-25° C.; evaporation of solvent was carried out using a rotary evaporator under reduced pressure (typically, 4.5-30 mmHg) with a bath temperature of up to 60° C.; the course of reactions was typically followed by TLC and reaction times are provided for illustration only; melting points are uncorrected; products exhibited satisfactory $^1$H-NMR and/or microanalytical data; yields are provided for illustration only; and the following conventional abbreviations are also used: mp (melting point), L (liter(s)), mL (milliliters), mmol (millimoles), g (grams), mg (milligrams), min (minutes), LC-MS (liquid chromatography-mass spectrometry) and h (hours), PS (polystyrene), DIE (diisopropylethylamine).

Example 1

Example 1 provides methods for preparing imidazole containing analogs according to Schemes A or B.

1.1.a Preparation of
1-bromo-3-(3,4-dichloro-phenyl)-propan-2-one, 2

To a solution of (3,4-Dichloro-phenyl)-acetyl chloride (29 mmol) and oxalyl chloride (44 mmol) in dichloromethane (100 mL) was added DMF (5 drops). The reaction solution started to evolve gas. The mixture was stirred for 4 h, concentrated in vacuo to give crude acid chloride. To the acid chloride was added anhydrous acetonitrile and THF (40 mL, 1:1); the mixture was cooled to 0° C. and trimethylsilyl diazomethane (54 mmol of 2.0 M in hexane) was added drop wise. The mixture was allowed to stand at −20° C. for 40 h and then warmed to room temperature and concentrated in vacuo. To the residue was added THF (40 mL), and the solution was cooled to 0° C. and excess aqueous HBr (48%) was added drop wise. The mixture was stirred for 1 h at 0° C., AcOEt was added and the organic phase was washed with brine, dried over MgSO$_4$, and concentrated in vacuo to give 1-bromo-3-(3,4-dichloro-phenyl)-propan-2-one, which was used without further purification.

MS m/z: 281 (M+1).

1.2.a Preparation of
4-(thiazol-2-ylsulfamoyl)-benzimidic acid ethyl ester, 5

A solution of 4-cyano-N-thiazol-2-yl-benzenesulfonamide (119 mmol) and 2-aminothiazole (119 mmol) in dichloromethane and pyridine (300 mL, 8:2) was stirred for 3 days. After concentrated in vacuo, the residue was diluted with ethyl acetate (500 mL) and the solution was washed with 1N HCl solution, sat NaHCO$_3$, dried over MgSO$_4$, and concentrated in vacuo. The residue was dissolved in ethanol (300 mL) and the solution was cooled to 0° C. To the cooled solution was bubbled through with HCl gas for 30 min and the resulting brown solution was placed in a refrigerator at −20° C. for three days and white precipitate was formed. After filtration, the white solid was washed with ethanol and dried in vacuo to give 4-(thiazol-2-ylsulfamoyl)-benzimidic acid ethyl ester (95 mmol) as hydrogen chloride salt.

$^1$H NMR (300 MHz, DMSO-d$_6$): δ 8.22 (d, J=8.4 Hz, 2H), 7.99 (d, J=8.4 Hz, 2H), 7.23 (d, J=4.6 Hz, 1H), 6.92 (d, J=4.6 Hz, 1H), 3.73 (q, J=7.2 Hz, 2H), 1.12 (t, J=7.1 Hz, 3H); MS m/z: 312 (M+1).

1.3.a Preparation of 4-(thiazol-2-ylsulfamoyl)-benzamidine, 6

A solution of 4-(thiazol-2-ylsulfamoyl)-benzimidic acid ethyl ester hydrochloride (100 mmol) in 7 N NH$_3$ (120 mL in methanol) was stirred at 60° C. for 2 h. After reaction mixture was cooled to room temperature, the precipitate was filtered, washed with methanol, and dried in vacuo to give a quantitative yield of 4-(thiazol-2-ylsulfamoyl)-benzamidine.

$^1$H NMR (300 MHz, DMSO-d$_6$): δ 8.86 (bs, J=4H), 7.92 (d, J=8.4 Hz, 2H), 7.86 (d, J=4.6 Hz, 1H), 6.98 (d, J=3.8 Hz, 1H), 6.56 (d, J=3.8 Hz, 1H); MS m/z: 283 (M+1).

1.4.a Preparation of 4-[4-(3,4-dichloro-benzyl)-1H-imidazol-2-yl]-N-thiazol-2-yl-benzenesulfonamide, 7

To a solution of 1-bromo-3-(3,4-dichloro-phenyl)-propan-2-one (4.1 mmol) in DMF (20 mL) was added sodium acetate (21 mmol) and the mixture was stirred for 2 hr at room temperature before concentrated ammonium hydroxide (5 mL) and ammonium chloride (1 g) were added. After the reaction mixture was stirred for 10 min, 4-(thiazol-2-ylsulfamoyl)-benzamidine (4.1 mmol) was added and the mixture was stirred at 60° C. overnight. After cooled to room temperature, the mixture was diluted with AcOEt (200 mL) and the resulting organic solution was washed with brine, dried over MgSO$_4$, and concentrated in vacuo. The crude product was purified by column chromatography to give 4-[4-(3,4-dichloro-benzyl)-1H-imidazol-2-yl]-N-thiazol-2-yl-benzenesulfonamide (3.1 mmol), which was converted to its sodium salt by reacting with NaOH solution (0.999 N).

$^1$H NMR (300 MHz, DMSO-d$_6$): δ 7.85 (d, J=8.4 Hz, 2H), 7.75 (d, J=8.4 Hz, 2H), 7.56-7.55 (m, 2H), 7.29 (d, J=8.3 Hz, 1H), 6.94 (s, 1H), 6.91 (d, J=3.8 Hz, 1H), 6.42 (d, J=3.8 Hz, 1H), 3.92 (s, 2H); MS m/z: 465 (M+1).

The following compounds were prepared using the same procedure:

$^1$H NMR (300 MHz, DMSO-d$_6$): δ 7.86 (d, J=8.5 Hz, 2H), 7.75 (d, J=8.5 Hz, 2H), 7.34 (s, 1H), 7.30-7.20 (m, 3H), 7.00 (s, 1H), 6.91 (d, J=3.8 Hz, 1H), 6.42 (d, J=3.8 Hz, 1H), 3.89 (s, 2H); MS m/z: 431 (M+1).

$^1$H NMR (300 MHz, DMSO-d$_6$): δ 7.86 (d, J=8.5 Hz, 2H), 7.77 (d, J=8.5 Hz, 2H), 7.44-7.34 (m, 2H), 7.30-7.20 (m, 2H), 6.92 (d, J=3.7 Hz, 1H), 6.43 (d, J=3.7 Hz, 1H), 3.98 (s, 2H); MS m/z: 449 (M+1).

$^1$H NMR (300 MHz, DMSO-d$_6$): δ 8.12 (d, J=8.7 Hz, 2H), 8.02 (d, J=8.7 Hz, 2H), 7.53 (s, 1H), 7.42-7.34 (m, 4H), 7.32 (d, J=4.6 Hz, 1H), 7.14 (t, J=7.3 Hz, 1H), 7.00 (d, J=8.6 Hz, 4H), 6.90 (d, J=4.6 Hz, 1H), 4.10 (s, 2H); MS m/z: 489 (M+1).

$^1$H NMR (300 MHz, DMSO-d$_6$): δ 8.10 (d, J=8.4 Hz, 2H), 8.02 (d, J=8.4 Hz, 2H), 7.62 (s, 1H), 7.47 (s, 1H), 7.39 (s, 2H), 7.31 (d, J=4.8 Hz, 1H), 6.90 (d, J=4.8 Hz, 1H), 3.10 (t, J=6.0 Hz, 2H), 2.96 (t, J=6.0 Hz, 2H); MS m/z: 479 (M+1).

1.5.a Preparation of 4-(5-methyl-4-phenyl-1H-imidazol-2-yl)-N-thiazol-2-yl-benzenesulfonamide, 10

To a solution of 4-formyl-benzenesulfonyl chloride (0.49 mmol) in dichloromethane and pyridine (5 mL, 4:1) was added thiazol-2-ylamine (0.49 mmol), and the resulting mixture was stirred for 1.5 h before it was concentrated in vacuo. The residue was suspended in concentrated ammonium hydroxide (5 mL) and 1-phenyl-propane-1,2-dione (0.49 mmol) was added. The mixture was stirred at 80° C. for 4 h before it was cooled to room temperature and concentrated in vacuo. The mixture was extracted with AcOEt and the organic phase was washed with brine, dried over MgSO$_4$, and concentrated in vacuo. The residue was purified by reverse phase HPLC to give 0.1 mmol of 4-(5-methyl-4-phenyl-1H-imidazol-2-yl)-N-thiazol-2-yl-benzenesulfonamide.

$^1$H NMR (300 MHz, DMSO-d$_6$): δ 8.19 (d, J=8.4 Hz, 2H), 8.05 (d, J=8.4 Hz, 2H), 7.71 (d, J=8.4 Hz, 2H), 7.06-7.44 (m, 3H), 7.22 (d, J=4.6 Hz, 1H), 6.96 (d, J=4.6 Hz, 1H), 2.51 (s, 3H); MS m/z: 397 (M+1).

Example 2

Example 2 provides methods for preparing triazole containing analogs according to Schemes C, D and E.

2.1.a Preparation of 4-[5-(3-Chloro-benzyl)-4H-[1,2,4]triazol-3-yl]-N-thiazol-2-yl-benzenesulfonamide, 13

To a solution of 4-(thiazol-2-ylsulfamoyl)-benzimidic acid ethyl ester (0.18 mmol) in ethanol (5 mL) was added hydrazine (0.1 mL) and the resulting mixture was stirred for 10 min. After the reaction mixture was concentrated in vacuo, it gave 4-(thiazol-2-ylsulfamoyl)-N-aminobenzamidine, which was used in next step without further purification. The crude 4-(thiazol-2-ylsulfamoyl)-N-aminobenzamidine was dissolved in THF and dichloromethane (10 mL, 1:1), and (3-chloro-phenyl)-acetyl chloride (0.36 mmol) and triethyl amine (0.9 mmol) were added. The mixture was stirred for 24 h before it was concentrated in vacuo. The mixture was diluted with AcOEt (30 mL) and the organic phase was washed with brine, dried over MgSO$_4$, and concentrated in vacuo. The solution of the residue in DMF and acetic acid (10 mL, 1:1) of was stirred at 80° C. for 24 h. After cooled to room temperature, the acetic acid was removed in vacuo and the residue was diluted with AcOEt (30 mL) and the organic phase was washed with brine, dried over MgSO$_4$, and concentrated in vacuo. The crude product was purified by reverse phase HPLC to give 4-[5-(3-chloro-benzyl)-4H-[1,2,4]triazol-3-yl]-N-thiazol-2-yl-benzenesulfonamide (0.05 mmol).

$^1$H NMR (300 MHz, DMSO-d$_6$): δ 14.20 (1H, bs), 12.80 (1H, bs), 8.12 (2H, d, J=8.4 Hz), 7.88 (2H, d, J=8.4 Hz), 7.27-7.41 (5H, m), 6.86 (1H, d, J=4.7 Hz), 4.19 (2H, bs); MS m/z: 432 (M+1).

2.2.a Preparation of 4-bromo-benzimidic acid ethyl ester, 15

A solution of 4-bromo-benzonitrile (58 mmol) in ethanol (200 mL) at 0° C. was bubbled through with HCl gas for 30 min and the resulting solution was stirred from 0° C. to room temperature over the weekend. After the reaction mixture was concentrated in vacuo, the residue was suspended in ether and the solid was filtered to give of 4-bromo-benzimidic acid ethyl ester as HCl salt (47 mmol).

MS m/z: 348 (M+1).

2.3.a Preparation of (3,4-dichloro-phenyl)-acetic acid methyl ester, 16

To a solution of (3,4-dichloro-phenyl)-acetic acid (90.5 mmol) in methanol (200 mL) was added trimethylsilylchloride (181 mmol) and the mixture was stirred overnight before it was concentrated. The residue was diluted with ether (200 mL) and the solution was washed with 1 N NaOH, brine, dried over $MgSO_4$, and concentrated in vacuo to give (3,4-dichloro-phenyl)-acetic acid methyl ester (90 mmol) as a colorless liquid.

MS m/z: 348 (M+1).

2.4.a Preparation of (3,4-dichloro-phenyl)-acetic acid hydrazide, 17

A solution of (3,4-dichloro-phenyl)-acetic acid methyl ester (44.7 mmol) and hydrazine (447 mmol) in ethanol (100 mL) was stirred at 80° C. for 18 h. After it was cooled to room temperature and concentrated in vacuo, the crude product was purified by crystallization in ethanol to give (3,4-dichloro-phenyl)-acetic acid hydrazide (43 mmol).

MS m/z: 348 (M+1).

2.5.a Preparation of 3-(4-bromo-phenyl)-5-(3-chloro-benzyl)-4H-[1,2,4]triazole, 18

To ethanol (50 mL) was added sodium metal (15.2 mmol). After sodium dissolved, 4-bromo-benzimidic acid ethyl ester HCl salt (15.2 mmol) was added to the solution, and the mixture ethanol was stirred at 80° C. for 2 days before it was concentrated. The residue was dissolved in DMF (60 mL) and concentrated acetic acid (200 mL) and the mixture was stirred at 80° C. for 16 h. After cooled to room temperature, the mixture was diluted with water (200 mL) and the resulting aqueous solution was extracted with AcOEt and the organic phase was washed with brine, dried over $MgSO_4$, and concentrated in vacuo. The crude product was purified by column chromatography to give 3-(4-bromo-phenyl)-5-(3-chloro-benzyl)-4H-[1,2,4]triazole (11.7 mmol).

$^1$H NMR (300 MHz, DMSO-$d_6$): δ 7.92 (2H, d, J=8.5 Hz), 7.68 (2H, d, J=8.5 Hz), 7.28 (4H, m), 4.15 (2H, s); MS m/z: 348 (M+1).

2.6.a Preparation of 3-(4-bromo-phenyl)-5-(3-chloro-benzyl)-4-methoxymethyl-4H-[1,2,4]triazole and 5-(4-bromo-phenyl)-3-(3-chloro-benzyl)-1-methoxymethyl-1H-[1,2,4]triazole (0.75 mmol), 19

To a suspension of NaH (1.1 mmol in 60% mineral oil) in THF (3 mL) at 0° C. was added 3-(4-bromo-phenyl)-5-(3-chloro-benzyl)-4H-[1,2,4]triazole (1.0 mmol). After the mixture was stirred for 30 min, MOMCl (1.0 mmol) was added and the mixture was stirred from 0° C. to room temperature overnight. The reaction mixture was diluted with EtOAc, washed with brine, dried over $MgSO_4$, and concentrated in vacuo. The crude product was purified by column chromatography to give 3-(4-bromo-phenyl)-5-(3-chloro-benzyl)-4-methoxymethyl-4H-[1,2,4]triazole and 5-(4-bromo-phenyl)-3-(3-chloro-benzyl)-1-methoxymethyl-1H-[1,2,4]triazole (0.75 mmol) as a mixture of two isomers (4:1).

MS m/z: 392 (M+1).

2.7.a Preparation of 3-(3-chloro-benzyl)-4-methoxymethyl-5-(4-triisopropylsilanylsulfanyl-phenyl)-4H-[1,2,4]triazole and 3-(3-chloro-benzyl)-1-methoxymethyl-5-(4-triisopropylsilanylsulfanyl-phenyl)-1H-[1,2,4]triazole, 20

To a suspension of NaH (1.5 mmol in 60% mineral oil) in THF (6 mL) at 0° C. was added triisopropylsilyl thiol (1.5 mmol) and the solution was stirred for 1 h before 3-(4-bromo-phenyl)-5-(3-chloro-benzyl)-4-methoxymethyl-4H-[1,2,4]triazole (1.5 mmol) in benzene (6 mL), triphenyl phosphine (0.6 mmol), and $Pd_2(dba)_3$ (0.08 mmol) were added. After bubbled argon through the solution for 15 min, the mixture was stirred at 80° C. for 18 h before it was cooled to room temperature. The reaction mixture was diluted with water (30 mL) and the resulting mixture was extracted with a solution of toluene and ethyl acetate (4:1) and the organic phase was washed with brine, dried over $MgSO_4$, and concentrated in vacuo. The crude product was purified by column chromatography to give 3-(3-chloro-benzyl)-4-methoxymethyl-5-(4-triisopropylsilanylsulfanyl-phenyl)-4H-[1,2,4]triazole and 3-(3-chloro-benzyl)-1-methoxymethyl-5-(4-triisopropylsilanylsulfanyl-phenyl)-1H-[1,2,4]triazole (1.0 mmol) as a mixture of two isomers (4:1).

MS m/z: 502 (M+1).

2.8.a Preparation of 4-[5-(3-chloro-benzyl)-4H-[1,2,4]triazol-3-yl]-N-thiazol-2-yl-benzenesulfonamide, 13

To a solution of 3-(3-chloro-benzyl)-4-methoxymethyl-5-(4-triisopropylsilanylsulfanyl-phenyl)-4H-[1,2,4]triazole (0.42 mmol) in acetonitrile (5 mL) at 0° C. was added potassium nitrate (1.05 mmol) and sulfuryl chloride, and the mixture was stirred for 1 h. The inorganic precipitate was filtered and washed with acetonitrile. The organic phase was concentrated and the residue was dissolved in THF (1.3 mL). To the solution were added thiazol-2-ylamine (0.5 mmol) and excess pyridine. The mixture was stirred over weekend. After concentration, the residue in 6N HCl (1 mL) and ethanol (1 mL) was stirred at 80° C. for 16 h before the reaction mixture was concentrated, the crude product was purified by reverse phase HPLC to give 4-[5-(3-chloro-benzyl)-4H-[1,2,4]triazol-3-yl]-N-thiazol-2-yl-benzenesulfonamide (0.1 mmol).

$^1$H NMR (300 MHz, DMSO-$d_6$): δ 14.20 (1H, bs), 12.12.80 (1H, bs), 8.12 (2H, d, J=8.4 Hz), 7.88 (2H, d, J=8.4 Hz), 7.27-7.41 (5H, m), 6.86 (1H, d, J=4.7 Hz), 4.19 (2H, bs); MS m/z: 432 (M+1).

2.9.a Preparation of 4-(5-diethoxymethyl-4H-[1,2,4]triazol-3-yl)-N-thiazol-2-yl-benzenesulfonamide, 13

A solution of 4-(thiazol-2-ylsulfamoyl)-benzimidic acid ethyl ester (0.60 mmol) and hydrazide (0.60 mmol) in DMF (2 mL) was stirred at 60° C. for 1 hour. An aqueous solution of 5 M potassium hydroxide was added, and the resulting mixture was stirred at 60° C. for 1 hour. The reaction mixture was quenched with 10 M of ammonium chloride (20 mL) and the aqueous phase was extracted with ethyl acetate. The combined organic layer was dried with magnesium sulfate, concentrated. The crude product was purified by column chromatography on silica gel to give pure product (0.43 mmol).

MS m/z: 410 (M+1).

Example 3

Example 3 provides methods for preparing benzimidazole containing analogs according to Scheme F.

3.1.a Preparation of 4-bromo-N-thiazol-2-yl-benzenesulfonamide, 22

A solution of 4-bromo-benzenesulfonyl chloride (100 mmol) and 2-aminothiazole (100 mmol) in dichloromethane and pyridine (300 mL, 8:2) was stirred for one day. After concentrated in vacuo, the residue was diluted with ethyl acetate (500 mL) and the solution was washed with 1N HCl solution, sat NaHCO$_3$, dried over MgSO$_4$, and concentrated in vacuo. The residue was recrystallized in ethyl acetate to give 4-bromo-N-thiazol-2-yl-benzenesulfonamide (85 mmol) as a white solid.

MS m/z: 319 (M+1).

3.2.a Preparation of 4-(H-benzoimidazol-2-yl)-N-thiazol-2-yl-benzenesulfonamide, 24

Benzimidazole (0.313 mmol) and MgO (0.376 mmol) was stirred in 1,4-dioxane (2 mL) for 10 min. at room temp. To the solution, copper iodide (0.627 mmol), palladium acetate (0.016 mmol), triphenylphosphine (0.062 mmol), and 4-bromo-N-thiazol-2-yl-benzenesulfonamide (0.313 mmol) were added. The reaction was sealed and heated to 150° C. After 7 h the reaction was cooled to 120° C. and stirred overnight. The reaction was cooled to room temperature and diluted with acetone. The solution was filtered through Celite and concentrated in vacuo. The crude was purified by reverse phase chromatography to yield 4-(1H-benzoimidazol-2-yl)-N-thiazol-2-yl-benzenesulfonamide (0.007 mmol).

MS m/z: 357 (M+1).

Example 4

Example 4 provides methods for preparing isoimidazole containing analogs according to Scheme G.

4.1.a Preparation of 4-acetyl-N-thiazol-2-yl-benzenesulfonamide, 26

A solution of 4-acetyl-benzenesulfonyl chloride (50 mmol) and 2-aminothiazole (50 mmol) in dichloromethane and pyridine (300 mL, 8:2) was stirred for one day. After concentrated in vacuo, the residue was diluted with ethyl acetate (500 mL) and the solution was washed with 1N HCl solution, sat NaHCO$_3$, dried over MgSO$_4$, and concentrated in vacuo. The residue was recrystallized in ethyl acetate to give 4-acetyl-N-thiazol-2-yl-benzenesulfonamide (35 mmol) as a yellow solid.

MS m/z: 283 (M+1).

4.2.a Preparation of 4-acetyl-N-methoxymethyl-N-thiazol-2-yl-benzenesulfonamide, 27

To a suspension of 4-acetyl-N-thiazol-2-yl-benzenesulfonamide (10 mmol) and potassium carbonate (15 mmol) in DMF (30 mL) was added chloro-methoxy-methane (10 mmol) and the mixture was stirred for 4 h. The reaction mixture was diluted with water (30 mL) and the resulting mixture was extracted with ethyl acetate. The organic phase was washed with brine, dried over MgSO$_4$, and concentrated in vacuo. The crude product was purified by column chromatography to give 4-cyano-N-methoxymethyl-N-thiazol-2-yl-benzenesulfonamide (5.2 mmol) as a white solid.

MS m/z: 327 (M$^+$+1).

4.3.a Preparation of 4-(2-bromo-acetyl)-N-methoxymethyl-N-thiazol-2-yl-benzenesulfonamide, 28

To a solution of 4-acetyl-N-thiazol-2-yl-benzenesulfonamide (10 mmol) in THF (50 mL) was added pyridinium tribromide (10 mmol), and the mixture was stirred for 4 h. The reaction mixture was diluted with water (30 mL) and the resulting mixture was extracted with ethyl acetate. The organic phase was washed with brine, dried over MgSO$_4$, and concentrated in vacuo. The crude product was purified by column chromatography to give 4-(2-bromo-acetyl)-N-methoxymethyl-N-thiazol-2-yl-benzenesulfonamide (8.2 mmol) as a white solid.

MS m/z: 327 (M$^+$+1).

4.4.a Preparation of 4-[2-(2,6-dichloro-benzyl)-3H-imidazol-4-yl]-N-methoxymethyl-N-thiazol-2-yl-benzenesulfonamide, 30

A solution of 4-(2-bromo-acetyl)-N-methoxymethyl-N-thiazol-2-yl-benzenesulfonamide (0.062 mmol) and the free base of 2-(2,6-dichloro-phenyl)-acetamidine (0.062 mmol) in DMF (2 mL) was heated to 80° C. for 2 h. After cooling to room temperature, the reaction mixture was purified by reverse phase chromatography to yield 4-[2-(2,6-dichloro-benzyl)-3H-imidazol-4-yl]-N-methoxymethyl-N-thiazol-2-yl-benzenesulfonamide (0.003 mmol).

MS m/z: 510 (M+1).

4.5.a Preparation of 4-[2-(2,6-dichloro-benzyl)-3H-imidazol-4-yl]-N-thiazol-2-yl-benzenesulfonamide, 31

A solution of 4-[2-(2,6-dichloro-benzyl)-3H-imidazol-4-yl]-N-methoxymethyl-N-thiazol-2-yl-benzenesulfonamide (0.003 mmol) in ethanol (1 mL) and 6 N HCl (1 mL) was heated to 80° C. for 5 h. The solution was cooled and purified by reverse phase chromatography to yield 4-[2-(2,6-dichloro-benzyl)-3H-imidazol-4-yl]-N-thiazol-2-yl-benzenesulfonamide TFA salt (0.003 mmol).

MS m/z: 465 (M+1).

Example 5

Example 5 provides methods for preparing pyrazole containing analogs according to Scheme H.

5.1.a Preparation of 4-cyano-N-methoxymethyl-N-thiazol-2-yl-benzenesulfonamide, 33

To a suspension of 4-cyano-N-thiazol-2-yl-benzenesulfonamide (10 mmol) and potassium carbonate (15 mmol) in DMF (30 mL) was added chloro-methoxy-methane (10 mmol) and the mixture was stirred for 4 h. The reaction mixture was diluted with water (30 mL) and the resulting mixture was extracted with ethyl acetate. The organic phase was washed with brine, dried over MgSO$_4$, and concentrated in vacuo. The crude product was purified by column chromatography to give 4-cyano-N-methoxymethyl-N-thiazol-2-yl-benzenesulfonamide (8.2 mmol) as a white solid.

MS m/z: 310 (M$^+$+1).

5.2.a Preparation of 4-formyl-N-methoxymethyl-N-thiazol-2-yl-benzenesulfonamide, 34

To a solution of 4-cyano-N-methoxymethyl-N-thiazol-2-yl-benzenesulfonamide (4.5 mmol) in THF (50 mL) at −78° C. under argon was added DIBAL (5.0 mmol, 1M in THF) and the solution was allowed to warm to room temperature overnight. After the reaction was quenched with potassium sodium tartrate solution slowly, the mixture was extracted with ethyl acetate, and the organic phase was washed with brine, dried over $MgSO_4$, and concentrated in vacuo. The crude product was purified by column chromatography to give 4-formyl-N-methoxymethyl-N-thiazol-2-yl-benzenesulfonamide (3.1 mmol).

MS m/z: 313 ($M^+$+1).

5.3.a Preparation of [5-(2,4-dichloro-phenoxy)-2-oxo-pentyl]-triphenyl-phosphonium; bromide, 35

A solution of triphenylphosphine (2.13 mmol) and 1-bromo-5-(2,4-dichloro-phenoxy)-pentan-2-one 2 (2.13 mmol) in toluene (20 mL) was stirred overnight. The solution was concentrated in vacuo to yield [5-(2,4-dichloro-phenoxy)-2-oxo-pentyl]-triphenyl-phosphonium; bromide (2.13 mmol) that was used without purification.

MS m/z: 507 ($M^+$).

5.4.a Preparation of 4-[6-(2,4-dichloro-phenoxy)-3-oxo-hex-1-enyl]-N-methoxymethyl-N-thiazol-2-yl-benzenesulfonamide, 36

[5-(2,4-Dichloro-phenoxy)-2-oxo-pentyl]-triphenyl-phosphonium; bromide (0.259 mmol) was dissolved in MeOH (10 mL). 1N NaOH was added drop wise until pH 9. The solution was then poured into water (100 mL). The solution was then extracted with EtOAc. The organic layer was washed brine, dried over $MgSO_4$ and concentrated in vacuo. Toluene (10 mL) was added followed by aldehyde 4-formyl-N-methoxymethyl-N-thiazol-2-yl-benzenesulfonamide (0.259 mmol). The solution was heated to 110° C. and stirred overnight. After cooling to 100° C., 1,4-dioxane (10 mL) was added. After stirring overnight the solution was concentrated in vacuo. The crude material was then filter through a plug of silica gel. The crude 4-[6-(2,4-dichloro-phenoxy)-3-oxo-hex-1-enyl]-N-methoxymethyl-N-thiazol-2-yl-benzenesulfonamide was used without further purification.

MS m/z: 541 (M+1).

5.5.a Preparation of 4-{5-[3-(2,4-dichloro-phenoxy)-propyl]-3,4-dihydro-2H-pyrazol-3-yl}-N-methoxymethyl-N-thiazol-2-yl-benzenesulfonamide, 37

4-[6-(2,4-Dichloro-phenoxy)-3-oxo-hex-1-enyl]-N-methoxymethyl-N-thiazol-2-yl-benzenesulfonamide (0.259 mmol) and hydrazine (2 mL) was heated to 80° C. in ethanol (15 mL) for 2 h. The solution was concentrated in vacuo. The crude 4-{5-[3-(2,4-dichloro-phenoxy)-propyl]-3,4-dihydro-2H-pyrazol-3-yl}-N-methoxymethyl-N-thiazol-2-yl-benzenesulfonamide was used without further purification.

MS m/z: 555 (M+1).

5.6.a Preparation of 4-{5-[3-(2,4-dichloro-phenoxy)-propyl]-2H-pyrazol-3-yl}-N-methoxymethyl-N-thiazol-2-yl-benzenesulfonamide, 38

A large excess of manganese oxide was added to 4-{5-[3-(2,4-dichloro-phenoxy)-propyl]-3,4-dihydro-2H-pyrazol-3-yl}-N-methoxymethyl-N-thiazol-2-yl-benzenesulfonamide (0.259 mmol) in chloroform (20 mL). After stirring for 4 h the solution was filtered thorough Celite and concentrated in vacuo. The crude 4-{5-[3-(2,4-dichloro-phenoxy)-propyl]-2H-pyrazol-3-yl}-N-methoxymethyl-N-thiazol-2-yl-benzenesulfonamide was used without further purification.

MS m/z: 553 (M+1).

5.7.a Preparation of 4-{5-[3-(2,4-dichloro-phenoxy)-propyl]-2H-pyrazol-3-yl}-N-thiazol-2-yl-benzenesulfonamide, 39

4-{5-[3-(2,4-Dichloro-phenoxy)-propyl]-2H-pyrazol-3-yl}-N-methoxymethyl-N-thiazol-2-yl-benzenesulfonamide (0.259 mmol) and 6 N HCl (1 mL) was heated to 80° C. in ethanol (1 mL) for 3 h. The solution was concentrated in vacuo. The crude material was purified by reverse phase chromatography to yield 4-{5-[3-(2,4-dichloro-phenoxy)-propyl]-2H-pyrazol-3-yl}-N-thiazol-2-yl-benzenesulfonamide (0.041 mmol) and 4-{5-[3-(2,4-dichloro-phenoxy)-propyl]-2H-pyrazol-3-yl}-N-methoxymethyl-N-thiazol-2-yl-benzenesulfonamide (0.024 mmol) was recovered.

MS m/z: 509 (M+1).

Example 6

Example 6 provides methods for preparing hydantoin containing analogs according to Scheme I.

6.1.a Preparation of 4-(2,5-dioxo-imidazolidin-4-yl)-N-methoxymethyl-N-thiazol-2-yl-benzenesulfonamide, 40

A mixture of 4-acetyl-N-methoxymethyl-N-thiazol-2-yl-benzenesulfonamide (0.45 mmol), potassium cyanate (1.53 mmol), and ammonium carbonate (4.5 mmol) in ethanol and water (5 mL, 1:1) was stirred at 135° C. in a microwave reactor for 10 min. The reaction mixture was quenched with 6N HCl aqueous solution. After neutralized with saturated $NaHCO_3$, the mixture was extracted with ethyl acetate. The organic phase was washed with brine, dried over $MgSO_4$, and concentrated in vacuo. The crude product was purified by reverse phase HPLC to give 4-(2,5-dioxo-imidazolidin-4-yl)-N-methoxymethyl-N-thiazol-2-yl-benzenesulfonamide (0.2 mmol).

MS m/z: 383 (M+1).

6.2.a Preparation of 4-(1-benzyl-2,5-dioxo-imidazolidin-4-yl)-N-thiazol-2-yl-benzenesulfonamide, 41

A suspension of 4-(2,5-dioxo-imidazolidin-4-yl)-N-methoxymethyl-N-thiazol-2-yl-benzenesulfonamide (0.1 mmol), benzyl bromide (0.2 mmol), and potassium carbonate (0.1 mmol) in DMF (5 mL) was stirred at 65° C. for 4 h. The reaction mixture was acidified with 6N HCl aqueous solution and was stirred for 30 min before neutralized with saturated $NaHCO_3$. The mixture was extracted with ethyl acetate and organic phase was washed with brine, dried over $MgSO_4$, and concentrated in vacuo. The crude product was purified by reverse phase HPLC to give 4-(1-benzyl-2,5-dioxo-imidazolidin-4-yl)-N-thiazol-2-yl-benzenesulfonamide (0.04 mmol).

MS m/z: 429 (M+1).

Example 7

Example 7 provides methods for preparing dihydrotriazolone containing analogs according to Schemes J and K.

7.1.a Preparation of N-{4-(Thiazol-2-ylsulfamoyl)-benzamidinyl}-N'-{3,4-Dichloro-benzyl}-urea, 43

A solution of 1,2-dichloro-4-isocyanato-benzene (0.177 mmol) and hydrazine (2.13 mmol) was stirred for 2 h in ethanol (5 mL) at room temperature. The solution was concentrated in vacuo and DMF (5 mL) was added followed by the addition of 4-(thiazol-2-ylsulfamoyl)-benzimidic acid ethyl ester (0.161 mmol). The solution was stirred for 3 days at room temperature. The reaction was concentrated in vacuo and that material was purification by reverse phase HPLC to yield N-{4-(thiazol-2-ylsulfamoyl)-benzamidinyl}-N'-{3,4-dichloro-benzyl}-urea (0.007 mmol).

MS m/z: 499 (M+1).

7.2.a Preparation of 4-[4-(3,4-dichloro-benzyl)-5-oxo-4,5-dihydro-1H-[1,2,4]triazol-3-yl]-N-thiazol-2-yl-benzenesulfonamide, 44

A solution of N-{4-(thiazol-2-ylsulfamoyl)-benzamidinyl}-N'-{3,4-dichloro-benzyl}-urea (0.177 mmol) in 1 N NaOH was heated to 95° C. overnight. The solution was acidified with 1 N HCl. The solution was then cooled to 0° C. in an ice bath. A precipitate was formed and collected by filtration. The solid was purification by reverse phase reverse phase HPLC to yield 4-[4-(3,4-dichloro-benzyl)-5-oxo-4,5-dihydro-1H-[1,2,4]triazol-3-yl]-N-thiazol-2-yl-benzenesulfonamide (0.003 mmol).

MS m/z: 482 (M+1).

7.3.a Preparation of 4-(thiazol-2-ylsulfamoyl)-N-(3,4-Dichloro-benzylideneamino)-benzamidine, 46

A solution of 4-(thiazol-2-ylsulfamoyl)-benzimidic acid ethyl ester (0.965 mmol) and hydrazine (0.5 mL) was stirred for 10 min. in ethanol (5 mL) at room temperature. The solution was concentrated in vacuo and DMF (5 mL) was added followed by the addition of 3,4-dichloro-benzaldehyde (1.06 mmol). Acetic acid (1 mL) was added and the solution was stirred for 2 h at room temperature. The solution was quenched with sat $NaHCO_3$, extracted with ethyl acetate, washed with brine and dried with $MgSO_4$. The reaction was concentrated in vacuo and that material was purification by column chromatography to yield 4-(thiazol-2-ylsulfamoyl)-N-(3,4-Dichloro-benzylideneamino)-benzamidine (0.39 mmol).

MS m/z: 454 (M+1).

7.4.a Preparation of 4-(thiazol-2-ylsulfamoyl)-N-(3,4-dichlorobenzylamino)-benzamidine, 47

A solution of 4-(thiazol-2-ylsulfamoyl)-N-(3,4-dichloro-benzylideneamino)-benzamidine (0.387 mmol) and NaCNBH$_3$ (large excess) was stirred in THF (5 mL) at room temperature. To the solution was added 6 N HCl drop wise until all starting material is consumed. The solution was quenched with sat $NaHCO_3$ and extracted with ethyl acetate. The organic phase was collected and concentrated in vacuo. The crude product was purification by reverse phase chromatography to yield 4-(thiazol-2-ylsulfamoyl)-N-(3,4-dichlorobenzylamino)-benzamidine (0.09 mmol).

MS m/z: 456 (M+1).

7.5.a Preparation of 4-[1-(3,4-dichloro-benzyl)-5-oxo-4,5-dihydro-1H-[1,2,4]triazol-3-yl]-N-thiazol-2-yl-benzenesulfonamide, 48

Ethyl chloroformate (0.05 mL) was added to a solution of 4-(thiazol-2-ylsulfamoyl)-N-(3,4-dichlorobenzylamino)-benzamidine (0.044 mmol) and TEA (0.20 mL) in THF (5 mL) at room temperature and the resulting solution was stirred for 2 h. After concentrating in vacuo 1 N NaOH (4 mL) was added and the solution was heated to 95° C. overnight. After the mixture was cooled to room temperature, the solution was acidified with 1 N HCl and freeze dried. The crude material was purification by reverse phase chromatography to yield 4-[1-(3,4-dichloro-benzyl)-5-oxo-4,5-dihydro-1H-[1,2,4]triazol-3-yl]-N-thiazol-2-yl-benzenesulfonamide (0.002 mmol).

MS m/z: 482 (M+1).

Example 8

Example 8 provides methods for testing the efficacy of the compounds of the invention.

8.1.a Cell Line Construction and Maintenance

Human Embryonic Kidney (HEK) cells were transfected with an hSCN3A construct using lipofectamine reagent (Invitrogen), using standard techniques. Cells stably expressing the hSCN3A constructs were identified by their resistance to G-418 (400 µg/ml). Clones were screened for expression using the whole-cell voltage-clamp technique.

8.2.a Cell Culture

HEK cells stably transfected with hSCN3A were maintained in DMEM medium supplemented with 10% heat-inactivated fetal bovine serum and 400 µg/ml G418 sulfate in an incubator at 37° C. with a humidified atmosphere of 10% $CO_2$. For HTS, cells were harvested from flasks by trypsinization and replated in an appropriate multi-well plate (typically 96 or 384 wells/plate) such that confluence would be achieved within 24 hours of plating. For electrophysiological studies, cells were removed from the culture flask by brief trypsinization and replated at low density onto glass cover slips. Cells were typically used for electrophysiological experiments within 24 to 72 h after plating.

8.3.a Electrophysiological Recording

Cover slips containing HEK cells expressing hSCN3A were placed in a bath on the stage of an inverted microscope and perfused (approximately 1 ml/min) with extracellular solution of the following composition: 138 mM NaCl, 2 mM $CaCl_2$, 5.4 mM KCl, 1 mM $MgCl_2$, 10 mM glucose, and 10 mM HEPES, pH 7.4, with NaOH. Pipettes were filled with an intracellular solution of the following composition: 135 mM CsF, 5 mM CsCl, 2 mM $MgCl_2$, 10 mM EGTA, 10 mM HEPES, pH 7.3 to 7.4, and had a resistance of 1 to 2 mega ohms. The osmolarity of the extracellular and intracellular solutions was 300 mmol/kg and 295 mmol/kg, respectively. All recordings were made at room temperature (22-24° C.) using AXOPATCH 200B amplifiers and PCLAMP software (Axon Instruments, Burlingame, Calif.) or PatchXpress 7000 hardware and associated software (Axon Instruments, Burlingame, Calif.).

hSCN3A currents in HEK cells were measured using the whole-cell configuration of the patch-clamp technique (Hamill et al., 1981). Uncompensated series resistance was typically 2 to 5 mega ohms and >85% series resistance compensation (50% for PatchXpress) was routinely achieved. As a result, voltage errors were negligible and no correction was applied. Current records were acquired at 20 to 50 KHz and filtered at 5 to 10 KHz.

The voltage-dependence of inactivation was determined by applying a series of depolarizing prepulses (8 sec long in 10 mV increments) from a negative holding potential. The voltage was then immediately stepped to 0 mV to assess the magnitude of the sodium current. Currents elicited at 0 mV were plotted as a function of prepulse potential to allow estimation of the voltage midpoint of inactivation ($V_{1/2}$). Cells were then voltage clamped at the empirically determined $V_{1/2}$.

Compounds were tested for their ability to inhibit hSCN3A sodium channels by activating the channel with a 20 ms voltage step to 0 mV from the empirically determined $V_{1/2}$. HEK cells stably transfected with hSCN3A were viewed under Hoffman contrast optics and placed in front of an array of flow pipes emitting either control or compound-containing extracellular solutions. In the cases where data were generated on the PatchXpress the onboard liquid handling facility of the instrument was used. All the compounds were dissolved in dimethyl sulfoxide to make 10 mM stock solutions, which were then diluted into bath solution to attain the final concentrations desired. The final concentration of dimethyl sulfoxide ($\leq$1% dimethyl sulfoxide) was found to have no significant effect on hSCN3A sodium currents.

8.4.a High-Throughput Screening Assays

Confluent cells in multi-well plates were incubated with a permeant radioactive ion ($^{22}$Na, $^{14}$C-guanidinium, etc) for 4-16 hours to allow uptake of the radiotracer. Excess radioactive ions were removed by washing with prewarmed buffer of the following composition: 138 mM NaCl, 2 mM $CaCl_2$, 5.4 mM KCl, 1 mM $MgCl_2$, 10 mM glucose, and 10 mM HEPES, pH 7.4, with NaOH. Efflux was initiated by addition of buffer containing any necessary chemical activators (e.g., 100 µM veratridine, 10-20 µg/ml Lqh scorpion venom, etc.). Various concentrations of test compounds or reference sodium channel blockers were added concurrently with the initiation of efflux. Efflux was allowed to progress for a defined period of time, typically 30-90 minutes, at 37° C. in a humidified 10% $CO_2$ atmosphere. Stimulated efflux was determined by collecting the extracellular solution and transferring to a multiwell plate for scintillation counting. Residual intracellular radioactivity was also determined by scintillation counting following lysis of the cells in the assay plate. Inhibition of efflux was determined by comparing efflux in the presence of test compounds to efflux in untreated control cells.

The activity of certain compounds of the present invention is set forth in Table II, below.

TABLE II

| Compound Number | NAME | SCN3A Inhibitory Activity |
|---|---|---|
| 11 | 4-{4-[3-(2,4-Dichloro-phenoxy)-propyl]-1H-imidazol-2-yl}-N-thiazol-2-yl-benzenesulfonamide | ++++ |
| 12 | 4-{4-[4-(4-Chloro-phenyl)-cyclohexyl]-1H-imidazol-2-yl}-N-thiazol-2-yl-benzenesulfonamide | ++++ |
| 13 | 4-[4-(2-Chloro-4-fluoro-benzyl)-1H-imidazol-2-yl]-N-thiazol-2-yl-benzenesulfonamide | ++++ |
| 16 | 4-[4-(3-Chloro-benzyl)-1H-imidazol-2-yl]-N-thiazol-2-yl-benzenesulfonamide | ++++ |
| 26 | 4-{4-[2-(3,5-Dichloro-phenyl)-ethyl]-1H-imidazol-2-yl}-N-thiazol-2-yl-benzenesulfonamide | ++++ |
| 36 | 4-[4-(3,4-Dichloro-benzyl)-1H-imidazol-2-yl]-N-thiazol-2-yl-benzenesulfonamide | ++++ |
| 42 | 4-[4-(4-Phenoxy-benzyl)-1H-imidazol-2-yl]-N-thiazol-2-yl-benzenesulfonamide | ++++ |
| 68 | 4-{4-[2-(3,5-Dichloro-phenyl)-ethyl]-5-iodo-1H-imidazol-2-yl}-N-thiazol-2-yl-benzenesulfonamide | ++++ |
| 95 | 4-[5-(3,4-Dichloro-benzyl)-4H-[1,2,4]triazol-3-yl]-N-thiazol-2-yl-benzenesulfonamide | ++++ |
| 114 | 4-[5-(4-Chloro-benzyl)-2H-[1,2,4]triazol-3-yl]-2-fluoro-n-thiazol-2-yl-benzenesulfonamide | ++++ |
| 122 | 5-Chloro-2-(4-{4-[2-(3,5-dichloro-phenyl)-ethyl]-1H-imidazol-2-yl}-benzenesulfonylmethyl)-thiazole | ++++ |
| 1 | 4-(4,5-Diphenyl-1H-imidazol-2-yl)-N-thiazol-2-yl-benzenesulfonamide | +++ |
| 3 | 4-(5-Benzhydryl-4H-[1,2,4]triazol-3-yl)-N-thiazol-2-yl-benzenesulfonamide | +++ |
| 6 | 4-(5-Benzhydryl-1H-imidazol-2-yl)-N-thiazol-2-yl-benzenesulfonamide | +++ |
| 7 | 4-[5-(3,5-Difluoro-benzyl)-1H-imidazol-2-yl]-N-thiazol-2-yl-benzenesulfonamide | +++ |
| 8 | 4-[5-(4-Chloro-benzyl)-1H-imidazol-2-yl]-N-thiazol-2-yl-benzenesulfonamide | +++ |
| 14 | 4-{4-[2-(2-Chloro-phenyl)-ethyl]-1H-imidazol-2-yl}-N-thiazol-2-yl-benzenesulfonamide | +++ |
| 15 | 4-{4-[2-(4-Fluoro-phenyl)-ethyl]-1H-imidazol-2-yl}-N-thiazol-2-yl-benzenesulfonamide | +++ |
| 18 | 4-{4-[2-(3-Chloro-4-methoxy-phenyl)-ethyl]-1H-imidazol-2-yl}-N-thiazol-2-yl-benzenesulfonamide | +++ |
| 19 | N-Thiazol-2-yl-4-{4-[2-(4-trifluoromethyl-phenyl)-ethyl]-1H-imidazol-2-yl}-benzenesulfonamide | +++ |
| 21 | N-Thiazol-2-yl-4-[4-(1-p-tolyl-cyclohexyl)-1H-imidazol-2-yl]-benzenesulfonamide | +++ |
| 22 | 4-{4-[2-(2,5-Bis-trifluoromethyl-phenyl)-ethyl]-1H-imidazol-2-yl}-N-thiazol-2-yl-benzenesulfonamide | +++ |
| 23 | 4-[4-(3,4-Difluoro-benzyl)-1H-imidazol-2-yl]-N-thiazol-2-yl-benzenesulfonamide | +++ |
| 25 | 4-{4-[1-(4-Chloro-phenyl)-cyclobutyl]-1H-imidazol-2-yl}-N-thiazol-2-yl-benzenesulfonamide | +++ |
| 27 | 4-[4-(3-Methyl-benzyl)-1H-imidazol-2-yl]-N-thiazol-2-yl-benzenesulfonamide | +++ |
| 28 | 4-{4-[2-(3-Chloro-phenyl)-ethyl]-1H-imidazol-2-yl}-N-thiazol-2-yl-benzenesulfonamide | +++ |
| 29 | 4-{4-[2-(2,5-Dimethyl-phenyl)-ethyl]-1H-imidazol-2-yl}-N-thiazol-2-yl-benzenesulfonamide | +++ |
| 34 | N-Thiazol-2-yl-4-[4-(4-trifluoromethyl-benzyl)-1H-imidazol-2-yl]-benzenesulfonamide | +++ |
| 47 | 4-[4-(Cyclohexyl-phenyl-methyl)-1H-imidazol-2-yl]-N-thiazol-2-yl-benzenesulfonamide | +++ |
| 51 | N-Thiazol-2-yl-4-[4-(2-trifluoromethyl-benzyl)-1H-imidazol-2-yl]-benzenesulfonamide | +++ |
| 96 | 4-[5-(3-Chloro-benzyl)-4H-[1,2,4]triazol-3-yl]-N-thiazol-2-yl-benzenesulfonamide | +++ |
| 115 | 4-[5-(2,6-Dichloro-phenoxymethyl)-2H-[1,2,4]triazol-3-yl]-2-fluoro-n-thiazol-2-yl-benzenesulfonamide | +++ |

TABLE II-continued

| Compound Number | NAME | SCN3A Inhibitory Activity |
|---|---|---|
| 116 | 4-[5-(3-Chloro-5-trifluoromethyl-pyridin-2-yl)-2H-[1,2,4]triazol-3-yl]-2-fluoro-n-thiazol-2-yl-benzenesulfonamide | +++ |
| 123 | 4-{5-[3-(2,4-Dichloro-phenoxy)-propyl]-1H-pyrazol-3-yl}-N-thiazol-2-yl-benzenesulfonamide | +++ |
| 4 | 4-(4-Methyl-5-phenyl-1H-imidazol-2-yl)-N-thiazol-2-yl-benzenesulfonamide | ++ |
| 9 | 4-{4-[3-(4-Chloro-phenoxy)-propyl]-1H-imidazol-2-yl}-N-thiazol-2-yl-benzenesulfonamide | ++ |
| 33 | N-Thiazol-2-yl-4-[4-(2-o-tolyl-ethyl)-1H-imidazol-2-yl]-benzenesulfonamide | ++ |
| 35 | 4-[4-(2-Fluoro-benzyl)-1H-imidazol-2-yl]-N-thiazol-2-yl-benzenesulfonamide | ++ |
| 43 | N-Thiazol-2-yl-4-[4-(3-trifluoromethoxy-benzyl)-1H-imidazol-2-yl]-benzenesulfonamide | ++ |
| 44 | 4-{4-[1-(4-Methoxy-phenyl)-cyclopropyl]-1H-imidazol-2-yl}-N-thiazol-2-yl-benzenesulfonamide | ++ |
| 49 | 4-(4-Benzo[1,3]dioxol-5-ylmethyl-1H-imidazol-2-yl)-N-thiazol-2-yl-benzenesulfonamide | ++ |
| 97 | 4-[5-(3,4-Dichloro-benzyl)-4-methoxymethyl-4H-[1,2,4]triazol-3-yl]-N-thiazol-2-yl-benzenesulfonamide | ++ |
| 117 | 4-[5-(3-Chloro-5-trifluoromethyl-pyridin-2-yloxymethyl)-2H-[1,2,4]triazol-3-yl]-n-thiazol-2-yl-benzenesulfonamide | ++ |
| 124 | 6-(2,2-Diphenyl-ethylamino)-pyridine-3-sulfonic acid thiazol-2-ylamide | ++ |
| 10 | 4-(1H-Benzoimidazol-2-yl)-N-thiazol-2-yl-benzenesulfonamide | + |
| 32 | 4-[4-(4-Methyl-benzyl)-1H-imidazol-2-yl]-N-thiazol-2-yl-benzenesulfonamide | + |
| 41 | 4-[4-(1-Phenyl-cyclopropyl)-1H-imidazol-2-yl]-N-thiazol-2-yl-benzenesulfonamide | + |
| 54 | 4-[4-(4-Methanesulfonyl-benzyl)-1H-imidazol-2-yl]-N-thiazol-2-yl-benzenesulfonamide | + |
| 98 | 4-[4-(3,5-Difluoro-benzyl)-1H-imidazol-2-yl]-N-thiazol-2-ylmethyl-benzenesulfonamide | + |
| 99 | 4-[3-(3,4-Dichloro-benzyl)-4-methyl-2,5-dioxo-imidazolidin-4-yl]-N-thiazol-2-yl-benzenesulfonamide | + |
| 100 | 4-[1-(3,4-Dichloro-benzyl)-4-methyl-2,5-dioxo-imidazolidin-4-yl]-N-thiazol-2-yl-benzenesulfonamide | + |
| 107 | 4-[4-(3,4-Dichloro-benzyl)-4-methyl-5-oxo-4,5-dihydro-1H-imidazol-2-yl]-N-thiazol-2-yl-benzenesulfonamide | + |
| 118 | N-thiazol-2-yl-4-[5-(5-trifluoromethyl-pyridin-2-yloxymethyl)-4H-[1,2,4]triazol-3-yl]-benzenesulfonamide | + |
| 119 | 4-[5-(2,6-Dichloro-phenoxymethyl)-2H-[1,2,4]triazol-3-yl]-n-thiazol-2-yl-benzenesulfonamide | + |
| 120 | 4-[5-(3,5-Dichloro-pyridin-2-yloxymethyl)-4H-[1,2,4]triazol-3-yl]-n-thiazol-2-yl-benzenesulfonamide | + |

Key:
+ indicates IC50 > 1 μM;
++ indicates 1 μM > IC50 > 0.5 μM;
+++ indicates 0.5 μM > IC50 > 0.1 μM;
++++ indicates IC50 < 0.1 μM While this invention has been disclosed with reference to specific embodiments, it is apparent that other embodiments and variations of this invention may be devised by others skilled in the art without departing from the true spirit and scope of the invention.

All patents, patent applications, and other publications cited in this application are incorporated by reference in their entirety.

What is claimed is:

1. A compound according to Formula I:

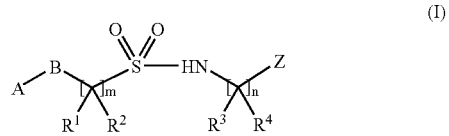

(I)

wherein $R^1$, $R^2$, $R^3$ and $R^4$ are members independently selected from H, F, $CF_3$, substituted or unsubstituted $C_1$-$C_4$ alkyl, unsubstituted 3- to 7-membered cycloalkyl and unsubstituted 3- to 7-membered heterocycloalkyl;

A is a member selected from:

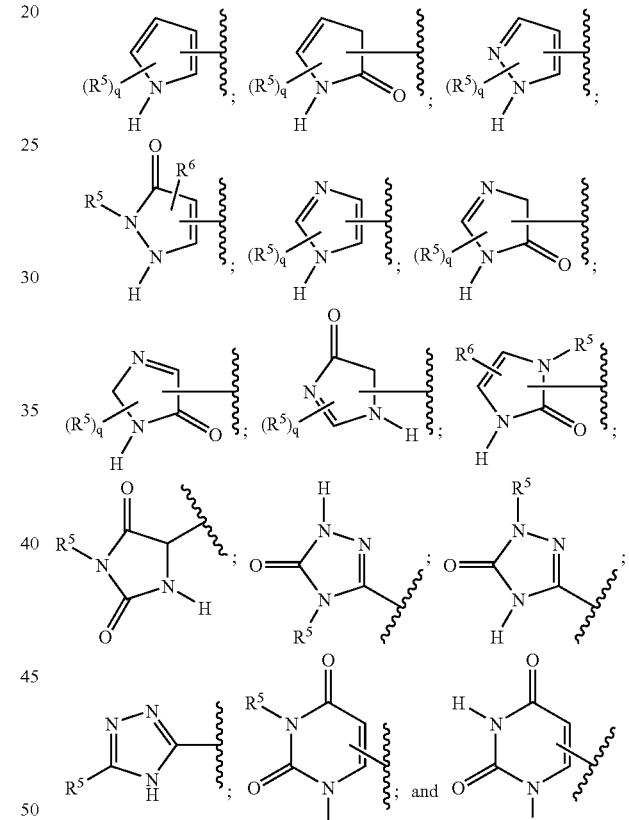

wherein $R^5$ is a member selected from substituted or unsubstituted $C_1$-$C_4$ alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl;

q is a member selected from the integers from 0 to 2;

$R^6$ is a member selected from H, halogen, $CF_3$, substituted or unsubstituted $C_1$-$C_4$ alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl;

B is a member selected from:

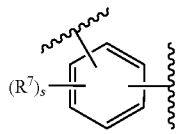

wherein
- s is an integer greater than 0, sufficient to satisfy the valence requirements of the ring atoms;
- each $R^7$ is a member independently selected from H, $OR^8$, $NR^9R^{10}$, $SO_2NR^9R^{10}$, cyano, halogen, $CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl;
- wherein
  - $R^8$ is a member selected from H, $CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl;
  - $R^9$ and $R^{10}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl;
- Z is a member selected from:

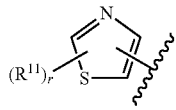

- wherein each $R^{11}$ is a member independently selected from H, $OR^{13}$, $NR^{14}R^{15}$, $SO_2NR^{14}R^{15}$, cyano, halogen, $CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl;
- wherein
  - $R^{13}$ is a member selected from H, $CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl;
  - $R^{14}$ and $R^{15}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl;
  - wherein
    - $R^{14}$ and $R^{15}$, together with the nitrogen to which they are bound, are optionally joined to form a substituted or unsubstituted 5- to 7-membered ring;
- r is a member selected from the integers from 0 to 2;

and

- m and n are independently selected from the integers from 0 to 2, such that when a member selected from m and n is greater than 1, each $R^1$ and $R^2$; $R^3$ and $R^4$, respectively, is independently selected.

2. The compound of claim 1, wherein m and n are 0.

3. The compound of claim 1, wherein A is a member selected from:

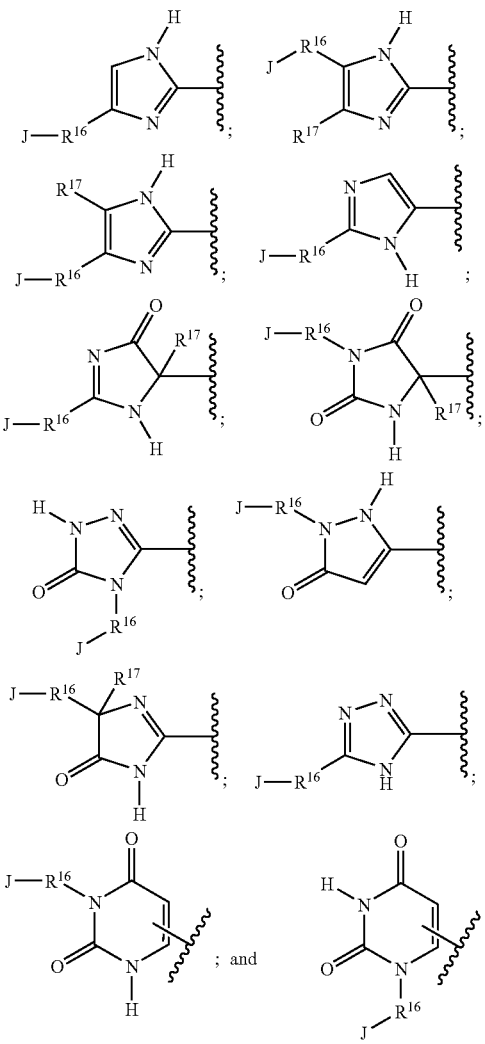

wherein
- J is a member selected from substituted or unsubstituted aryl and substituted or unsubstituted heteroaryl;
- $R^{16}$ is a member selected from a bond, substituted or unsubstituted alkylene, substituted or unsubstituted cycloalkylene, substituted or unsubstituted heterocycloalkylene, substituted or unsubstituted heteroalkylene, substituted or unsubstituted arylene and substituted or unsubstituted heteroarylene; and
- $R^{17}$ is a member selected from H, halogen, $CF_3$, substituted or unsubstituted $C_1$-$C_4$ alkyl, an unsubstituted 4- to 7-membered cycloalkyl ring and an unsubstituted 4- to 7-membered heterocycloalkyl ring.

4. The compound of claim 3, wherein J-R$^{16}$ has the formula:

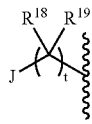

wherein
R$^{18}$ and R$^{19}$ are members independently selected from H, substituted or unsubstituted alkyl, substituted or unsubstituted heteroalkyl, and substituted or unsubstituted aryl
wherein
R$^{18}$ and R$^{19}$, together with the carbon to which they are attached, are optionally joined to form a member selected from a substituted or unsubstituted 3- to 7-member cycloalkyl moiety and substituted or unsubstituted 5- to 7-member heterocycloalkyl moiety; and
t is an integer selected from 0 to 4, such that when t is greater than 1, each R$^{18}$ and R$^{19}$ is independently selected.

5. The compound of claim 3, having the formula:

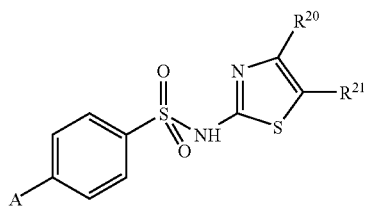

wherein
R$^{20}$ and R$^{21}$ are members independently selected from is a member independently selected from H, OR$^{22}$, NR$^{23}$R$^{24}$, SO$_2$NR$^{23}$R$^{24}$, cyano, halogen, CF$_3$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl
wherein
R$^{22}$ is a member selected from H, CF$_3$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl; and
R$^{23}$ and R$^{24}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl
wherein
R$^{23}$ and R$^{24}$, together with the nitrogen to which they are bound, are optionally joined to form a substituted or unsubstituted 5- to 7-membered ring.

6. The compound of claim 1, having inhibitory activity against a voltage-gated sodium channel.

7. A pharmaceutical formulation comprising the compound of claim 1.

8. A method of modulating activity of a sodium channel in a subject, said method comprising:
administering to said subject an amount of the compound of claim 1 sufficient to modulate said activity.

9. A method of ameliorating or alleviating a condition in a subject, wherein said condition is a member selected from pain, irritable bowel syndrome, Crohn's disease, epilepsy, seizures, multiple sclerosis, bipolar depression and tachyarrhythmias, said method comprising:
administering to said subject an amount of the compound of claim 1 sufficient to ameliorate or alleviate said condition.

10. The method according to claim 9, wherein said condition is pain, and said pain is a member selected from acute pain, chronic pain, visceral pain, inflammatory pain and neuropathic pain.

11. The compound of claim 1, wherein the compound has the formula:

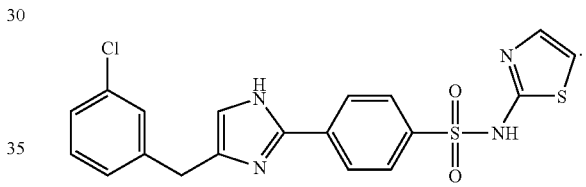

12. The compound of claim 1, wherein A is

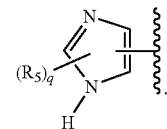

13. The compound of claim 1, wherein A is

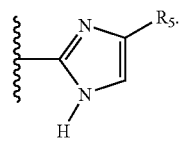

* * * * *

UNITED STATES PATENT AND TRADEMARK OFFICE
CERTIFICATE OF CORRECTION

Page 1 of 1

PATENT NO.       : 7,615,569 B2
APPLICATION NO.  : 11/464057
DATED            : November 10, 2009
INVENTOR(S)      : Fulp et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 364 days.

Signed and Sealed this
Eighteenth Day of January, 2011

David J. Kappos
*Director of the United States Patent and Trademark Office*